United States Patent [19]
Nagayoshi et al.

[11] Patent Number: 5,179,934
[45] Date of Patent: Jan. 19, 1993

[54] ENDOSCOPE

[75] Inventors: Mitsugu Nagayoshi; Atsushi Miyazaki; Hirofumi Miyanaga, all of Hachioji; Sakae Takehana, Machida; Hideyuki Adachi, Hachioji; Yasuhiro Ueda, Kokubunji; Eiichi Fuse; Yoshisada Aoki, both of Hachioji, all of Japan

[73] Assignee: Olympus Optical Co., Ltd., Tokyo, Japan

[21] Appl. No.: 655,678

[22] Filed: Feb. 14, 1991

[30] Foreign Application Priority Data

Feb. 20, 1990 [JP] Japan .................. 2-39018
Nov. 1, 1990 [JP] Japan .................. 2-293518
Nov. 9, 1990 [JP] Japan .................. 2-305185

[51] Int. Cl.$^5$ ............................ A61B 1/00
[52] U.S. Cl. ............................ 128/4
[58] Field of Search .......... 128/4, 6; 604/95

[56] References Cited

U.S. PATENT DOCUMENTS

| | | | |
|---|---|---|---|
| 4,794,912 | 1/1989 | Lia | 128/4 |
| 4,832,473 | 5/1989 | Ueda | 350/506 |
| 4,890,602 | 1/1990 | Hake | 128/4 |
| 4,962,751 | 10/1990 | Kravter | 128/4 |
| 5,014,515 | 5/1991 | Kravter | 128/4 X |
| 5,018,506 | 5/1991 | Danna et al. | 128/4 |

FOREIGN PATENT DOCUMENTS

0304380A2 2/1989 European Pat. Off. .
1-110241 4/1989 Japan .

Primary Examiner—Paul J. Hirsch
Assistant Examiner—Thomas Price
Attorney, Agent, or Firm—Frishauf, Holtz, Goodman & Woodward

[57] ABSTRACT

An endoscope comprises an insertion section, and this insertion section has a distal end portion, a proximal end portion, and a bendable portion located between the distal and proximal end portions. A fluid-pressure actuator is coupled to the insertion section, so as to bend the bendable portion. The fluid-pressure actuator is made up of an extensible body and an expansion-restricting member. The extensible body defines an internal space and has an extension axis along which it extends or contracts. The expansion-restricting member causes the extensible body to extend in the direction of the extension axis when a fluid is supplied into the internal space, and causes the extensible body to contract in the direction of the extensible axis when the fluid is discharged from the internal space. The bendable portion of the insertion section is bent in accordance with the extension or contraction of the extensible body.

35 Claims, 21 Drawing Sheets

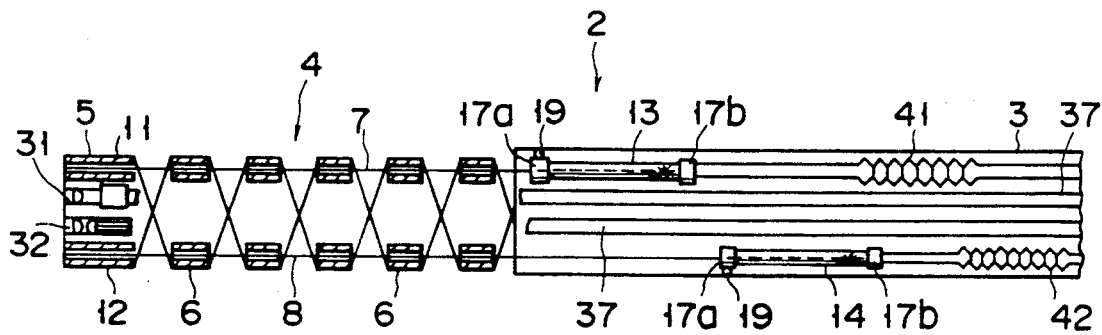
F I G. 7
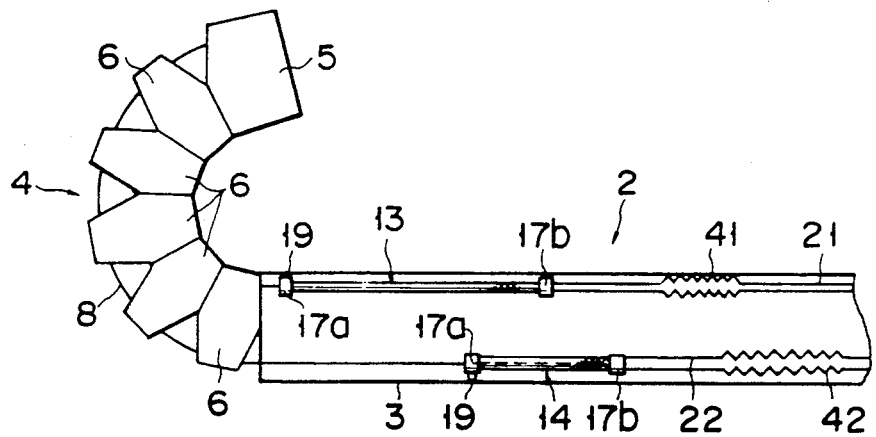
F I G. 8
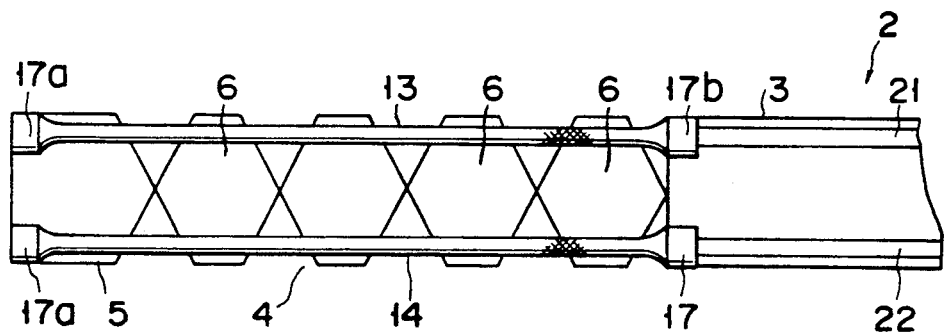
F I G. 9

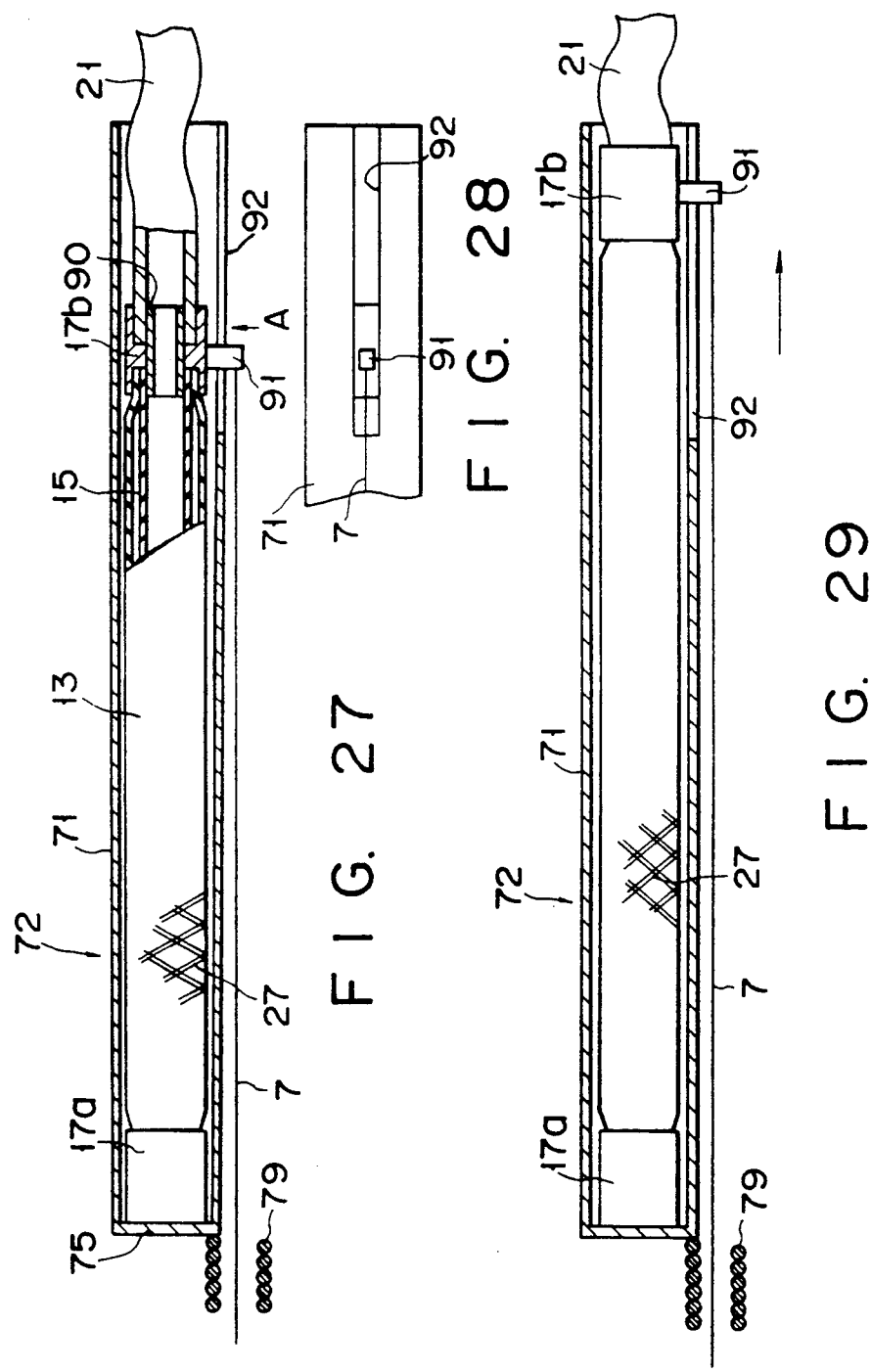

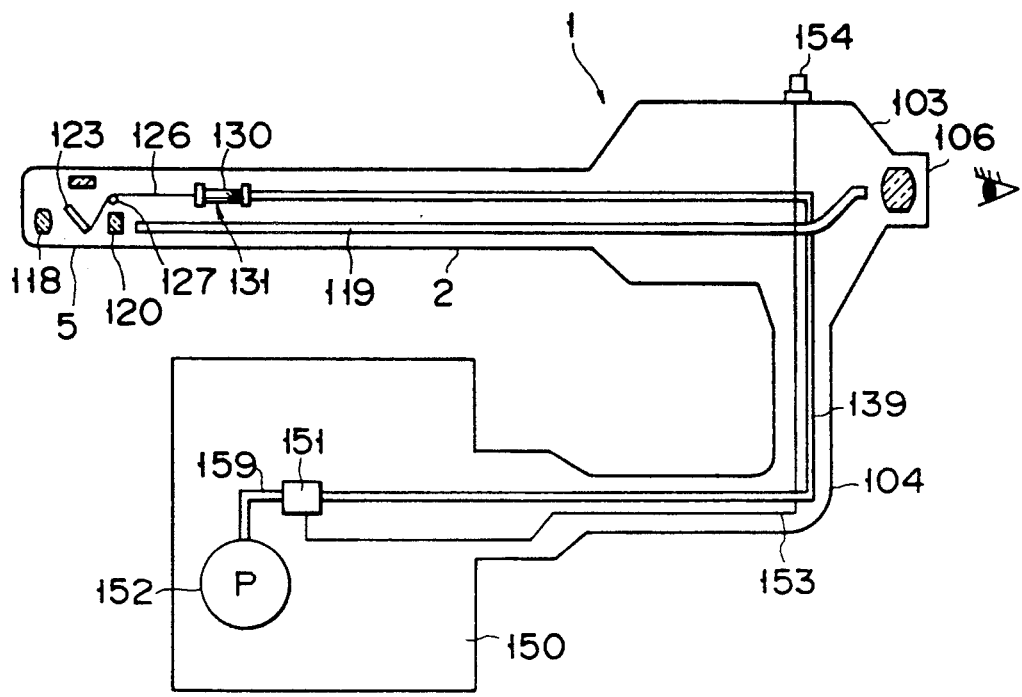
F I G. 33
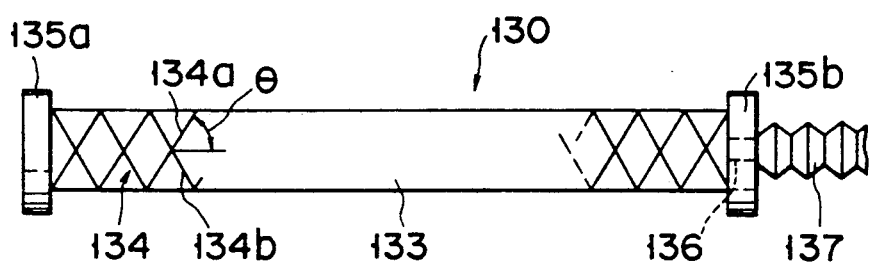
F I G. 34

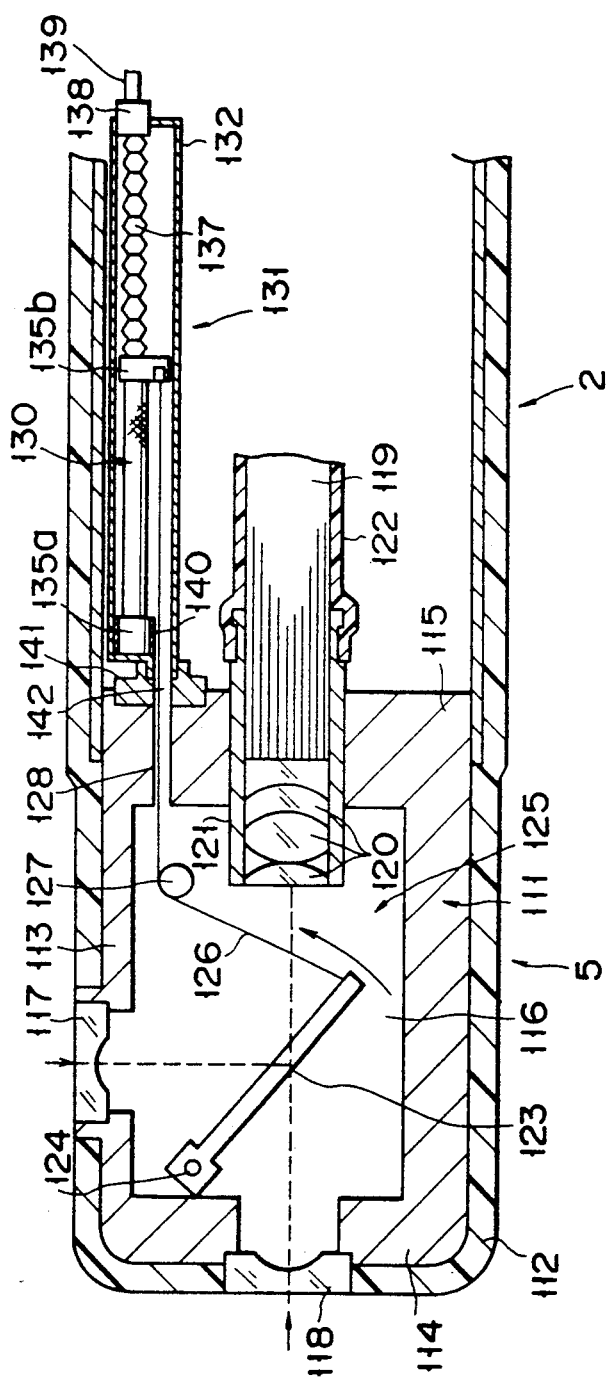
F I G. 35

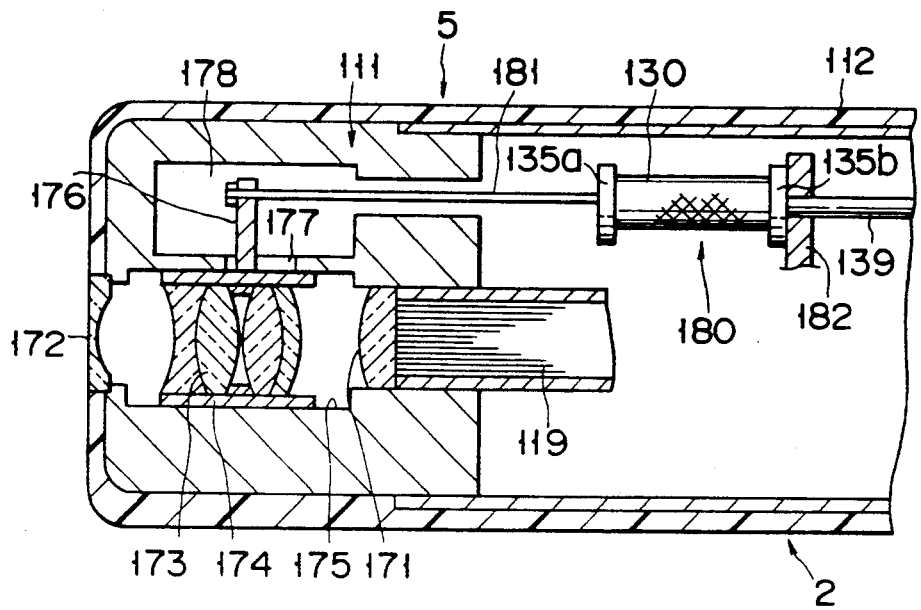
F I G. 38
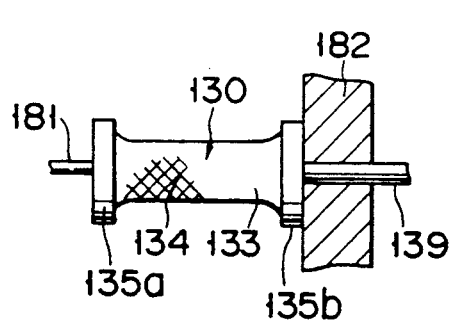 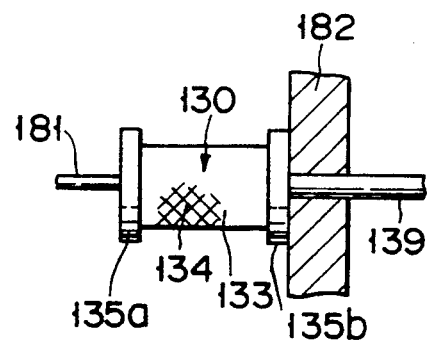
F I G. 39A   F I G. 39B

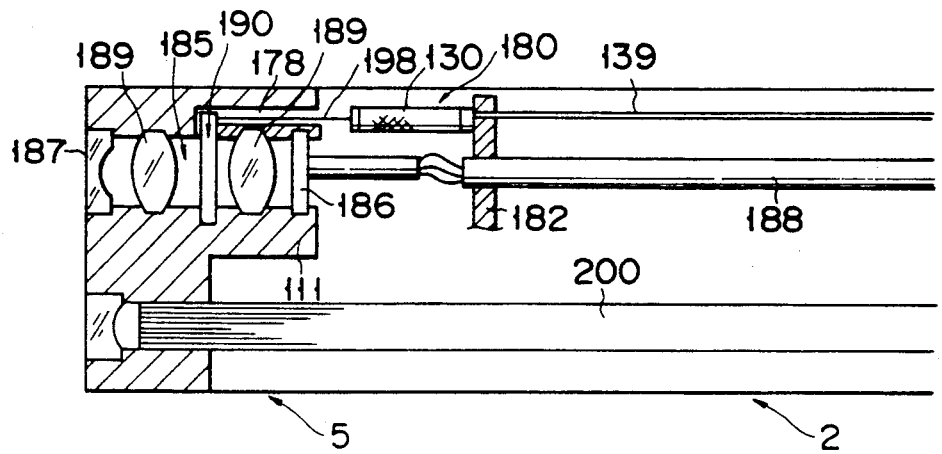
F I G. 40
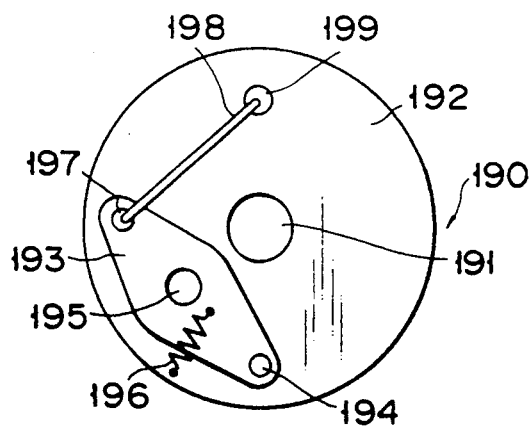
F I G. 41A
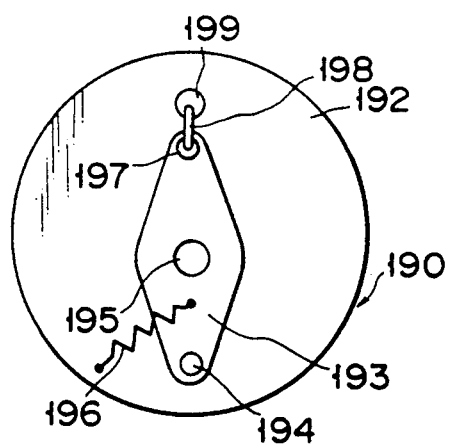
F I G. 41B

ENDOSCOPE

BACKGROUND OF THE INVENTION

1. Field of the Invention

The present invention relates to an endoscope comprising a fluid-pressure actuator which can extend or contract in response to the supply or discharge of a fluid.

2. Description of the Related Art

U.S. Pat. No. 4,794,912 discloses an endoscope which employs a fluid-pressure actuator to forcibly bend the bendable portion of the insertion section thereof. The fluid-pressure actuator is comprised of an elastic tube, and a flexible mesh tube fitted around the elastic tube and made by inextensible filaments. When a fluid is supplied into the elastic tube of the actuator, the tube expands in the radial direction thereof, and thus contracts in the longitudinal direction thereof (in short, the tube shortens). As a result, a bendable portion-operating wire is pulled, and the bendable portion is bent or curved, accordingly.

The above fluid-pressure actuator greatly expands in the radial direction when its elastic tube is supplied with a fluid to operate the bendable portion. To incorporate the actuator in the insertion section, therefore, it is necessary to determine the actuator's installation space in consideration of the maximum diameter of the actuator.

When the hydraulic-pressure actuator expands in response to the supply of a fluid into the elastic tube, it may happen that the actuator will touch or strongly press some other structural component arranged inside the insertion section. This problem can be solved by employing a cover or the like, but the size of such a cover has to be determined in consideration of the maximum diameter of the actuator, and the actuator's installation space has to be widened, accordingly. Since the size of the insertion section is determined by the diameter of the portion in which the actuator and cover are contained the insertion section is inevitably large.

The fluid-pressure actuator can be used for operating a mirror by which to change the vision field of the objective optical system of the endoscope. In this case as well, the insertion section of the endoscope is inevitably large.

SUMMARY OF THE INVENTION

Accordingly, an object of the present invention is to provide an endoscope incorporating a fluid-pressure actuator which is compact in size and which is driven with a simple driving mechanism.

To achieve this object, the present invention provides an endoscope comprising:

an elongated insertion section including a distal end portion, a proximal end portion, and a bendable portion located between the distal and proximal end portions;

a fluid-pressure actuator, coupled to the insertion section, for bending the bendable portion, the fluid-pressure actuator including: (a) an extensible body defining an internal space and having an extension axis along which the extensible body extends or contracts; and (b) expansion-restricting means for restricting expansion of the extensible body, the expansion-restricting means causing the extensible body to extend in the direction of the extension axis when a fluid is supplied into the internal space, and causing the extensible body to contract in the direction of the extensible axis when the fluid i discharged from the internal space;

conversion means for converting the extension or contraction of the fluid-pressure actuator into a bending motion of the bendable portion of the insertion section; and fluid supply/discharge means for supplying the fluid into the internal space of the extensible body or discharging the fluid from the internal space.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 7 is a partially-sectional schematic side view of an insertion section employed in the second embodiment of the present invention;

FIG. 8 is a side view showing how the bendable portion of the insertion section of the second embodiment is bent;

FIG. 9 is a schematic side view of an insertion section employed in the third embodiment of the present invention;

FIG. 27 is a longitudinally-sectional view of a fluid-pressure actuator of the ninth embodiment;

FIG. 28 shows how a portion of the fluid-pressure actuator of the ninth embodiment looks like when viewed in the direction indicated by arrow A in FIG. 27;

FIG. 29 is a longitudinally-sectional view of the fluid-pressure actuator of the ninth embodiment;

FIG. 33 is a schematic explanatory view of an endoscope's insertion section incorporating a fluid-pressure actuator according to the twelfth embodiment of the present invention;

FIG. 34 is a side view of the fluid-pressure actuator of the twelfth embodiment;

FIG. 35 is a longitudinally-sectional view of the distal end portion and the neighboring portion of the endoscope's insertion section of the twelfth embodiment;

FIG. 38 is a longitudinally-sectional view of the distal end portion and the neighboring portion of the endoscope's insertion section employed in the thirteenth embodiment of the present invention;

FIG. 39A is a side view showing an extended state of a fluid-pressure actuator employed in the thirteenth embodiment;

FIG. 39B is a side view showing a non-pressurized state of the actuator of the thirteenth embodiment;

FIG. 40 is a longitudinally-sectional view which shows the distal end portion of the endoscope's insertion section employed in the fourteenth embodiment of the present invention, the distal end portion being shown along with its neighboring regions;

FIGS. 41A and 41B are front views of a diaphragm device employed in the fourteenth embodiment;

DETAILED DESCRIPTION OF THE PREFERRED EMBODIMENTS

Figure 1:
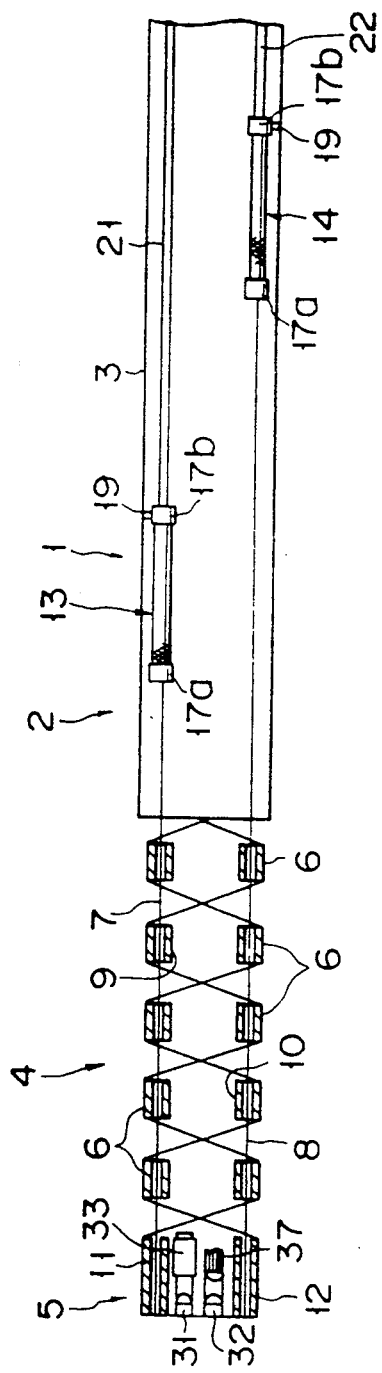
FIG. 1 is a schematic side view of an insertion section employed in the first embodiment of the present invention.

The first embodiment of the present invention will now be described, with reference to FIGS. 1 through 6. As is shown in FIG. 1, the insertion section 2 of an endoscope 1 is comprised of a flexible tube portion 3, a bendable portion 4 and a distal end portion 5. These portions are arranged from the proximal end of the insertion section 2 to the distal end thereof in the order mentioned, and are coupled together. The bendable portion 4 has a plurality of bending pieces 6. Each bending piece 6 has upper and lower wire guides 9 and 10, and operating wires 7 and 8 used for bending the bendable portion 4 are inserted into the upper and lower wire guides 9 and 10, respectively. The operating wires 7 and 8 constitute driving force-transmitting members and will be detailed later. The bending pieces 6 constitute conversion means; they are applied with a driving force transmitted through the operating wires 7 and 8, and bend the bendable portion 4 in accordance with the driving force. The distal end portion 5 is coupled to the bending piece 6 arranged at the distal end of the bendable portion 4.

The distal end portion 5 has a pair of pipe-like wire receivers 11 and 12. These wire receivers 11 and 12 extend along the axis of the distal end portion 5 in opposition to each other, and are open at the proximal ends thereof. The operating wires 7 and 8 are inserted into the wire receivers 11 and 12, respectively, and are fixed inside the wire receivers 11 and 12 by fixing means, e.g. by soldering.

The upper and lower operating wires 7 and 8, which are fixed inside the wire receivers 11 and 12 and inserted through the wire guides 9 and 10, respectively, are coupled to respective artificial muscles or fluid-pressure actuators 13 and 14 incorporated in the flexible tube portion 3. The fluid-pressure actuators 13 and 14 are shifted from each other in the axial direction of the insertion section 2.

Figure 2A:
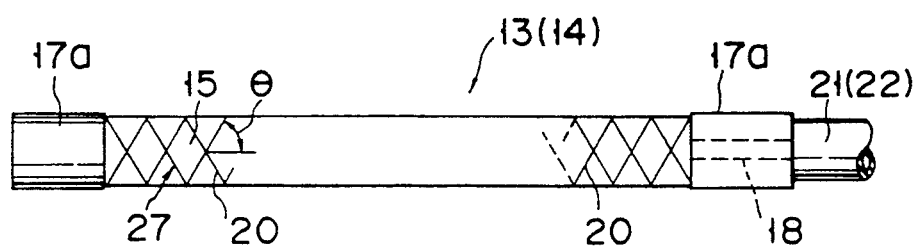
FIG. 2A is a side view of a fluid pressure type fluid-pressure actuator employed in the first embodiment.
Figure 2B:
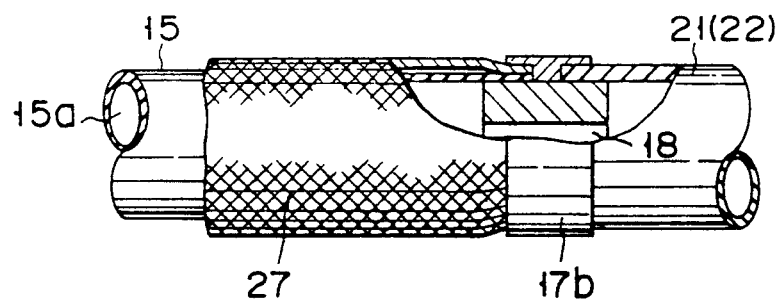
FIG. 2B is a partially-cutaway enlarged view of an end portion of the fluid-pressure actuator.

As is shown in FIG. 2B, each of the fluid-pressure actuators 13 and 14 is made up of a tubular elastic member 15 (i.e., an expansible body), which is formed of rubber or the like, and a reinforcing mesh member 27 which covers the elastic member 15. The front and rear open ends of each actuator are hermetically sealed by sealing members 17a and 17b, respectively. The rear sealing member 17b has a hole 18 which communicates with the inner space 15a of the actuator. Flexible fluid supply/discharge tubes 21 and 22, through which a fluid is supplied or discharged, are connected to the holes 18 of the sealing members 17b of the actuators 13 and 14, respectively.

Each reinforcing mesh member 27 is obtained by interlacing warp and weft strands of inextensible element wires 20 in a plain weave manner, for example, in such a manner that the interlaced warp and weft strands constitute a tubular structure. The interlacing angle $\theta$ which each element wire 20 (a warp strand or a weft strand) forms with reference to the longitudinal axis of the actuator is set to be greater than 54° 44', normally within the range of 65° to 80°. The angle which is formed between a warp strand and a weft strand is $2\theta$. Without the mesh members 27, the fluid-pressure actuators 13 and 14 would radially expand, when their internal spaces are supplied with a fluid through the tubes 21 and 22. However, such radial expansion is restricted by the mesh members 27, and the actuators 13 and 14 extend in the axial direction thereof. That is, the reinforcing members 27 serve as means for restricting expansion of the elastic members 15.

The fluid-pressure actuators 13 and 14 are coaxial with the operating wires 7 and 8, respectively. The sealing member 17b at the rear end of each actuator is fixed to the inner wall of the flexible tube portion 3 by means of a fixing member 19. The front end of each actuator is a free end. The rear ends of the operating wires 7 and 8 are connected to the sealing members 17a located at the front ends of the actuators 13 and 14, respectively.

The operating wires 7 and 8 are flexible more or less, but are rigid to such an extent that they can transmit a pushing force produced by the extension of the actuators 13 and 14's. It is preferable that each operating wire be made by a solid wire of stainless steel, a solid wire of Ni-Ti alloy having ultra-elasticity, or an oppressed type coil sheath of such material.

The flexible fluid supply/discharge tubes 21 and 22, which communicate with the inner spaces of the respective fluid-pressure actuators 13 and 14, extend through the interior of the insertion section 2 and are led out of the endoscope 1. In the outside of the endoscope 1, the tubes 21 and 22 are connected to a compressor 24 through respective directional control valves 23. The directional control valves 23 controls the fluid pressure which is to be applied to the internal spaces of the actuators 13 and 14 through the tubes 21 and 22. The directional control valves 23 are controlled by a control device 25, and an operating device 26 is connected to the control device 25.

In the distal end portion 5 of the insertion section 2, an objective lens 31 used for observation and a lens 32 used for illumination are arranged. A solid-state imaging element 33 (e.g. charge coupled device is located at the focal point of the objective lens 31. As is understood in FIG. 3, a signal produced by the solid-state imaging element 33 is supplied, through a signal line 34, to a camera control unit 35, by which the signal is converted into an image signal. A monitor 36 for displaying an observation image is connected to the camera control unit 35. The illumination lens 32 is connected to the distal end of a light guide fiber 37 inserted in the insertion section 2. The proximal end of the light guide fiber 37 is connected to a light source device 38.

The illumination light emitted from the light source device 38 is transmitted to the illumination lens 32 through the light guide fiber 37, and the observation field of the endoscope 1 is illuminated with the illumination light coming from the illumination lens 32.

A description will now be given of the operation of the endoscope system mentioned above.

The operator operates the operating device 26 and causes the control device 25 to control the directional control valves 23 in such a manner that pressurized air is supplied from the compressor 24 to one of the fluid-pressure actuators 13 and 14 through the fluid supply/exhaust tube 21 or 22. In this case, a one-pitch portion of the tubular elastic member 15 is applied, in the axial direction of the elastic member 15, with the force given below:

$$\{F + (\pi/4)D^2p\}$$

where P represents an internal pressure exerted on the actuators 13 and 14, and D represents an inner diameter of the tubular elastic members 15. The one-pitch portion is a portion determined by that distance L for which the element wire 20 is shifted in the axial direction of the elastic members 15 after making one turn.

In the circumferential direction of the elastic member 15, the one-pitch portion of the elastic member 15 is applied with the force given below:

$$(DLP)/2$$

Figure 6:
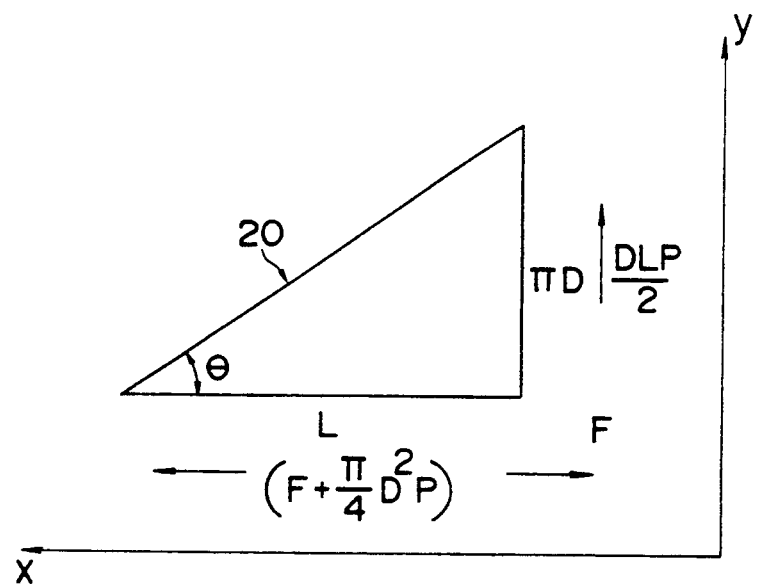
FIG. 6 is a graph showing how the fluid-pressure actuator employed in the first embodiment operates.

The state where the above forces are applied to the elastic member 15 is shown in FIG. 6. In consideration of the balance of the forces in the x-axis direction, the following formula is obtained:

$$F = (\pi/4)D^2p\{(2/\tan^2\theta) - 1\}$$

This formula can be expanded as follows:

$$F = (\pi/4)D^2p(2/\tan^2\theta) - (\pi/4)D^2p$$

Figure 5:
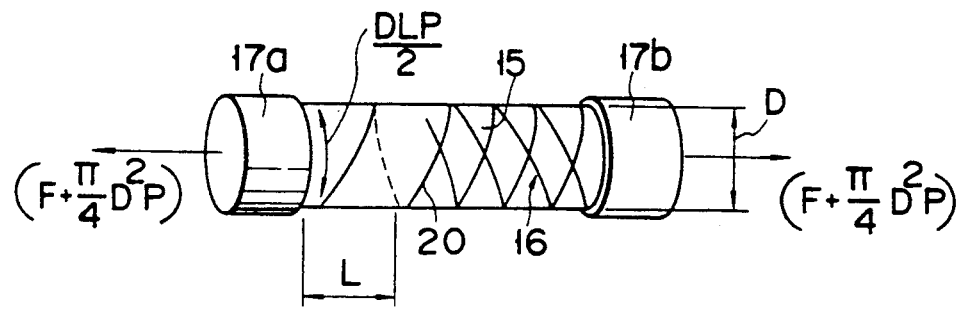
FIG. 5 is a perspective view showing how the fluid-pressure actuator employed in the first embodiment operates.

In consideration of this expanded formula and FIGS. 5 and 6, it can be understood that $(x/4)D^2p$ expresses an extension force and $(x/4)D^2p(2/\tan^2\theta)$ expresses a contraction force. That is, the fluid-pressure actuators 13 and 14 produce a contraction force when the value of F is positive, and produce an extension force when the value of F is negative. Since, as mentioned above, the interlacing angle $\theta$ which each element wire 20 (a warp strand or a weft strand) forms with reference to the longitudinal axis of the actuator is set to be greater than 54° 44', the value of F is always negative.

As is understood from the above, when the fluid-pressure actuator 13 (14) is applied with a fluid pressure, it is subjected to an extension force, so that it extends in the axial direction. It extends in the forward direction only, since the sealing members 17b at its rear end is fixed to the inner wall of the tube portion 3, as mentioned above.

The extension force is transmitted through the operating wire 7 (8) to both the tip end of the bendable portion 4 and the distal end portion 5. Thus, the bendable portion 4 is bent, accordingly. The fluid-pressure actuators 13 and 14 are secured such that they do not overlap with each other even when one of them extends axially.

Figure 4:
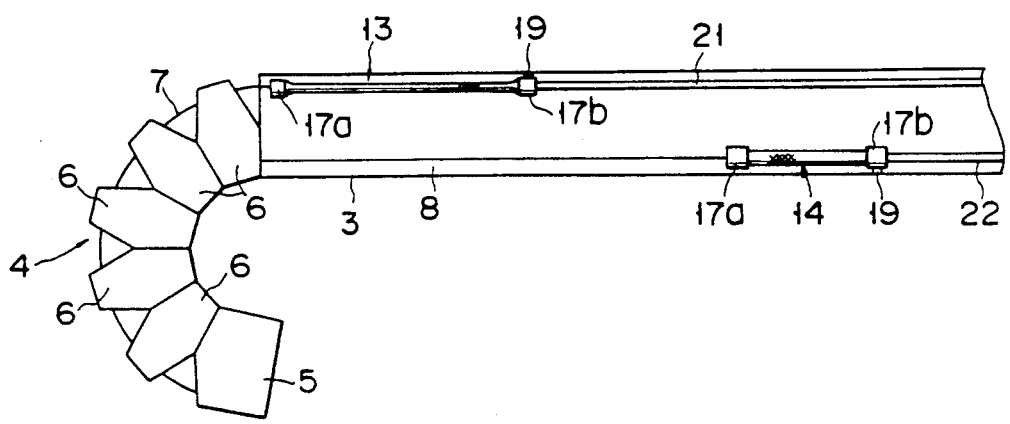
FIG. 4 is a side view showing how the bendable portion of the insertion section of the first embodiment is bent.

In the case where the fluid-pressure actuator 13 located in the upper region of the flexible tube portion 3 extends, as is shown in FIG. 4, the operating wire 7 pushes the distal end portion 5 forward, so that the bendable portion 4 is bent downward. Since, at the time, the wire guides 9 of the bending pieces 6 prevent the operating wire 7 from buckling or slacking, the extension force is reliably transmitted to the distal end portion 5. If necessary, guide means made by coil sheaths may be provided to prevent the operating wires from buckling or slacking in a more reliable manner.

It should be noted that two more fluid-pressure actuators may be arranged inside the insertion section 2, in addition to the actuators 13 and 14 mentioned above. In this case, the bendable portion 4 can be bent in four directions.

The second embodiment of the present invention will now be described, with reference to FIGS. 7 and 8.

In the second embodiment, the sealing members 17a located at the front end of the fluid-pressure actuators 13 and 14 are fixed to the inner wall of the flexible tube portion 3 by means of the coupling members 19, and the rear end of each actuator is made to function as a free end. The proximal ends of the operating wires 7 and 8 are connected to the respective sealing members 17b located at the rear end (free end) of the actuators 13 and 14, and the operating wires 7 and 8 are inserted through the interiors of the respective actuators 13 and 14. The fluid supply/discharge tubes 21 and 22, which communicate with the inner spaces of the respective actuators 13 and 14, have bellows 41 and 42 at intermediate points thereof, respectively. These bellows 41 and 42 are arranged as close as possible to the actuators 13 and 14. Each of the operating wires 7 and 8 is constituted by a stranded wire of stainless steel. As for the other structures, the second embodiment is similar to the first embodiment According to the second embodiment, the operator operates the operating device 26 and causes the control device 25 to control the directional control valves 23 in such a manner that pressurized air is supplied from the compressor 24 to on of the fluid-pressure actuators 13 and 14 through the fluid supply/exhaust tube 21 or 22. In this case, the actuator into which the pressurized air is supplied begins to extend, as in the first embodiment. Since, in the second embodiment, the sealing member 17a located at the front end of the fluid-pressure actuator is fixed to the inner wall of the flexible tube portion 3, the actuator extends in the backward direction only. As a result of the backward extension of the actuator, the operating wire connected to the actuator pulls the distal end structure 5, thus bending the bendable portion 4.

In the second embodiment, the sealing member 17a at the front end of the fluid-pressure actuator is fixed to the inner wall of the flexible tube portion 3, so that the actuator extends in the backward direction only, and the fluid supply/discharge tube communicating with the inner space of the actuator is compressed. As is shown in FIG. 8, however, the bellows 41 or 42 absorbs the extension of the actuator.

In the second embodiment, the operating wires 7 and 8 are pulled by the extension of the actuators 13 and 14, and the bendable portion 4 is bent by the pulling force of the operating wires 7 and 8. With this structure, the operating wires 7 and 8 never slack, and a sufficient force with which to bend the bendable portion 4 can be transmitted in a reliable manner.

Figure 10:
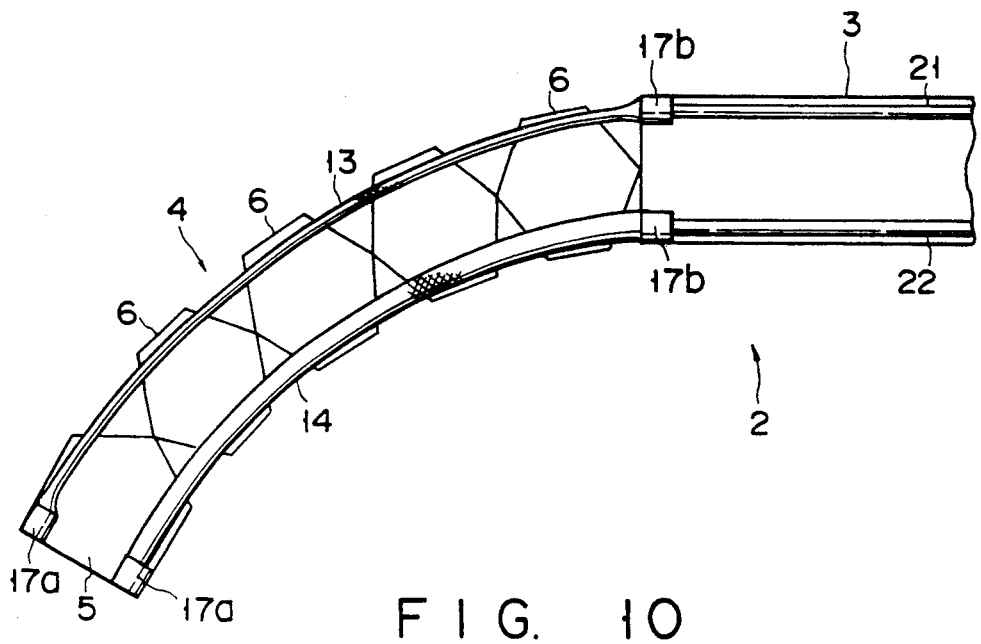
FIG. 10 is a side view showing how the bendable portion of the insertion section of the third embodiment is bent.

The third embodiment of the present invention will now be described, with reference to FIGS. 9 and 10.

In the third embodiment, no operating wire is employed, and the fluid-pressure actuators 13 and 14 are made to function as operating wires as well.

The actuators 13 and 14 employed in the third embodiment have a similar structure to that of the actuators employed in the foregoing embodiments, and are arranged throughout the bendable portion 4 in opposition to each other. The sealing members 17a located at the front end of the actuators 13 and 14 are fixed to the inner wall of a member disposed in the distal end portion 5. Further, the sealing members 17b located at the rear end of the actuators 13 and 14 are also fixed to the inner wall of the tip end of the flexible tube portion 3. The actuators 13 and 14 are fixed such that their lengths are substantially ½ of the maximal lengths when, as is shown in FIG. 9, the bendable portion 4 is straight. As for the other structures, the third embodiment is similar to the first embodiment.

According to the third embodiment, when one of the actuators 13 (or 14) is supplied with a fluid through the corresponding fluid supply/discharge tube 21 (or 22), the actuator supplied with the fluid extends in the axial direction thereof. In accordance with the axial extension of the actuator 13 (or 14), the distal end portion 5 is pushed in the forward direction, thus bending the bendable portion 4.

When one of the actuators 13 (or 14) extends, the other actuator is compressed. In order to prevent this compressed actuator from slacking, the corresponding directional control valve 23 is controlled by the control device 25 such that a fluid is discharged from the compressed actuator. The fluid is discharged from the compressed actuator until the length of the actuator become equal to the length obtained when no fluid is supplied. The actuators 13 and 14 in this state is shown in FIG. 10.

Figure 11:
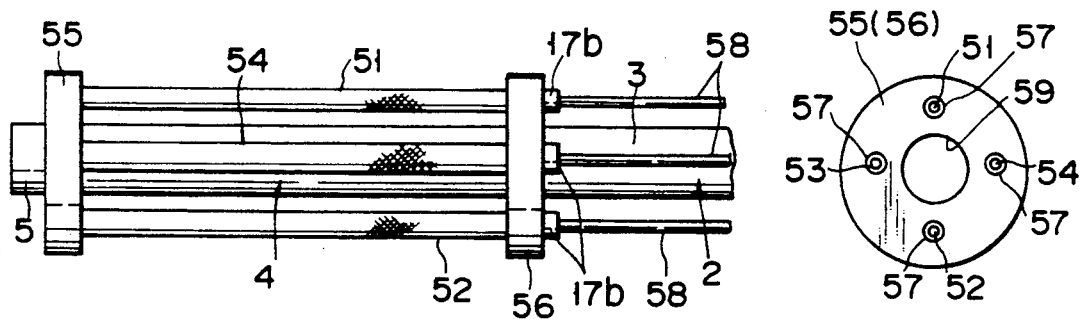
FIG. 11 is a schematic side view of an insertion section and a fluid-pressure actuator-assembling structure employed in the fourth embodiment of the present invention.
Figure 12:
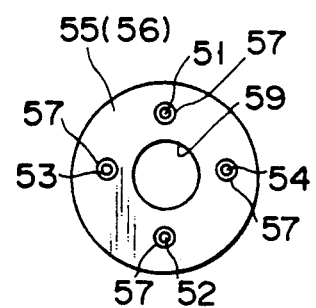
FIG. 12 is a front view of the fluid-pressure actuator assembling structure employed in the fourth embodiment of the present invention.
Figure 13:
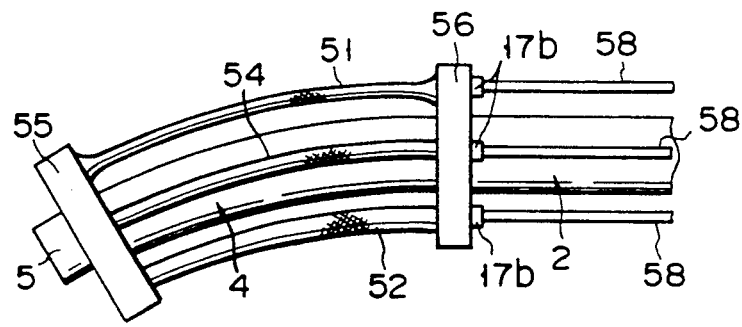
FIG. 13 is a side view showing how the bendable portion of the insertion section of the fourth embodiment is bent.

The fourth embodiment of the present invention will now be described, with reference to FIGS. 11-13.

In the fourth embodiment, an actuator-driving device is provided independently of the insertion section; it is not provided inside the insertion section 2, as in the foregoing embodiments. More specifically, four fluid pressure type artificial muscles, namely fluid-pressure actuators 51, 52, 53 and 54, are provided between the distal end portion 5 and the flexible tube portion 3 such that they are located at regular intervals around the outer circumference of the insertion section 2. A ring member 55 is fixed to the outer circumference of the distal end portion 5; likewise, a ring member 56 is fixed to the outer circumference of the tip end of the flexible tube portion 3. The four actuators 51-54 are secured by these two ring members 55 and 56. It should be noted that the actuator-driving device is detachable from the insertion section 2.

Each of the ring member 55 and 56 has an opening 59, and the inner diameter of this opening 59 corresponds to the outer diameter of the member around which the opening 59 is fitted. With the insertion section 2 being fitted in the opening 59, the ring members 55 and 56 can be arranged at arbitrary positions.

The fluid-pressure actuators 51-54 are stretched between the two ring members 55 and 56. Each of these ring member 55 and 56 has four fixing holes 57, and these fixing holes 57 are formed at regular intervals in the circumferential direction of the ring member. The fixing holes 57 are fitted around the respective sealing members 17a or 17b of the actuators 51-54. In other words, the sealing members 17a located at the front ends of the actuators 51-54 are securely fitted into the fixing holes 57 of the front ring member 55, while the r sealing members 17b located at the rear ends of the actuators 51-54 are securely fitted into the fixing holes 56 of the rear ring member 56.

In the bendable portion 4, the four fluid-pressure actuators 51-54 are arranged at regular intervals around the outer circumference of the insertion section 2 such that a certain clearance is provided between the actuators 51-54 and the insertion section 2. The actuators 51-54 are connected to the respective fluid supply/discharge tubes 58.

As for the structures not mentioned above, the fourth embodiment is similar to the foregoing embodiments.

According to the fourth embodiment, one of two actuator pairs (i.e., upper and lower actuators 51 and 52, and right and left actuators 53 and 54) is selected, and a fluid is supplied into one of the selected actuator pair from the corresponding fluid supply/discharge tube 58. The actuator supplied with the fluid and extends in the axial direction thereof. Since, therefore, the ring members 55 and 56 are pushed by the axial extension of that actuator, the bendable portion 4 is bent, accordingly. This state is shown in FIG. 13.

The actuator opposing that actuator which is supplied with the fluid is compressed, due to the bending motion of the bendable portion. In order to prevent this compressed actuator from slacking, the corresponding directional control valve 23 is controlled by the control device 25 such that a fluid is discharged from the compressed actuator. The fluid is discharged from the compressed actuator until the length of the actuator become equal to the length obtained when no fluid is supplied.

The fluid-pressure actuators of the fourth embodiment are advantageous, in that they can be easily applied to the insertion section of a conventional endoscope of any type. No particular design change is required for this application.

The fifth embodiment of the present invention will now be described, with reference to FIGS. 14 and 15.

The fifth embodiment differs from the first embodiment in the manner in which fluid-pressure actuators 13 and 14 are arranged inside the flexible tube portion 3 of the insertion section 2.

According to the fifth embodiment, the fluid-pressure actuators 13 and 14 are connected to the respective operating wires 7 and 8 as follows. First, the actuators 13 and 14 are lengthened until their lengths become ½ of the maximal lengths. In this state, the lengths of the operating wires 7 and 8 are adjusted, and then the operating wires 7 and 8 are fixed to the respective actuators 13 and 14. This state is shown in FIG. 14. When the insertion section 2 is straight, the tubular elastic member 15 of each actuator is stretched. As for the other structures, the fifth embodiment is similar to the first embodiment.

Figure 14:
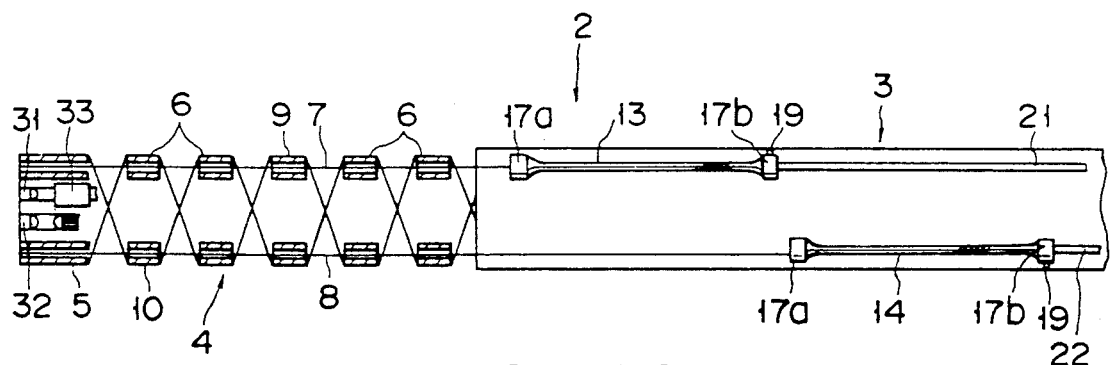
FIG. 14 is a partially-sectional schematic side view of an insertion section employed in the fifth embodiment of the present invention.
Figure 15:
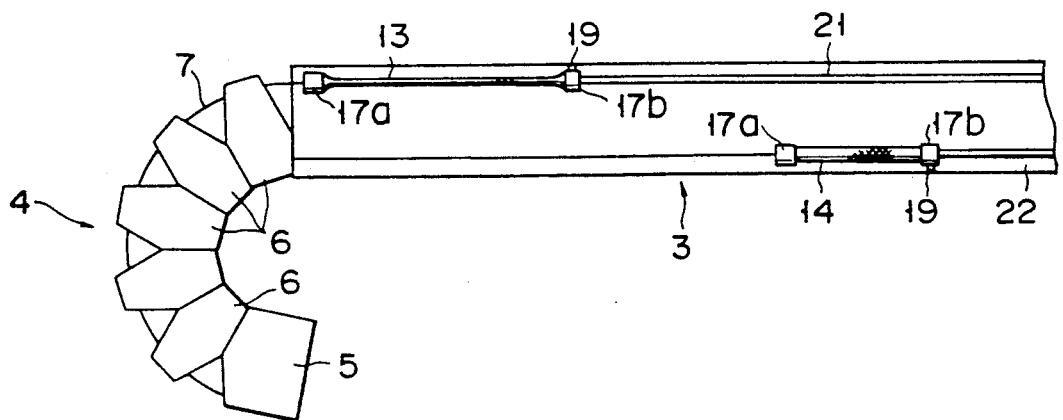
FIG. 15 is a side view showing how the bendable portion of the insertion section of the fifth embodiment is bent.

When, in the state shown in FIG. 14, a fluid is discharged from the lower fluid-pressure actuator 14, the tubular elastic member 15 of this actuator 14 restores its original shape because of the elasticity thereof. Simultaneous with this, a fluid is added to the upper actuator 13, so that the upper actuator 13 extends in the axial direction. As is understood from this, one of the wires 7 and 8 is pulled by the actuator which contracts when restoring its original shape, and the bendable portion 4 is bent, accordingly.

In the fifth embodiment, the bendable portion 4 is bent, with one of the operating wires 7 and 8 being pulled. Unlike the case where the operating wires are pushed, the operating wires 7 and 8 do not buckle. In addition, the actuators 13 and 14 do not fold or buckle since they contract when restoring their original shapes. Therefore, a large driving force can be produced, and reliable bending of the bendable portion 4 is ensured.

The sixth embodiment of the present invention will now be described, with reference to FIGS. 16 and 17.

In the sixth embodiment, the upper operating wire 7 is connected to a tension coil spring 61, while the lower operating wire 8 is connected to a fluid-pressure actuator 62, which is similar in structure to the actuators employed in the foregoing embodiments. By use of the tension coil spring 61 and the fluid-pressure actuator 62, the bendable portion 4 of the insertion section is bent upward or downward. More specifically, the tension coil spring 61 is stretched and, in this stretched state, its one end is connected to the rear end of the upper operating wire 7. The other end of the tension coil spring 61 is fixed to the inner wall of the flexible tube portion 3. As for the other structure, the sixth embodiment is similar to the first embodiment.

Figure 16:
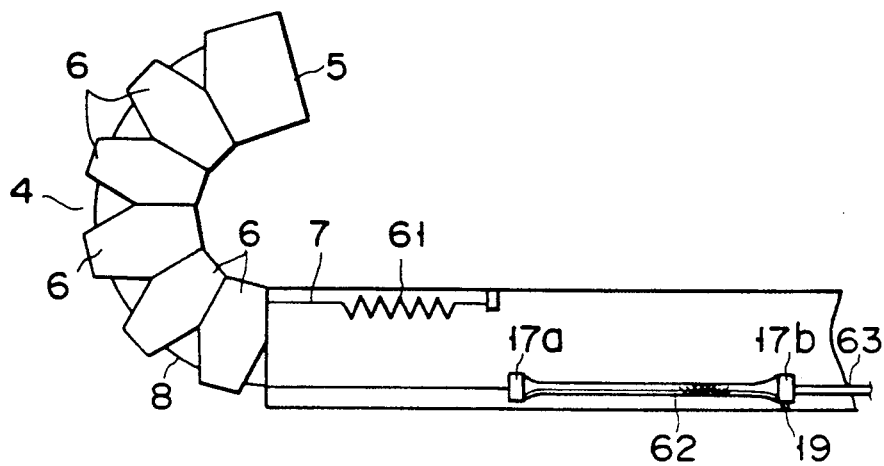
FIG. 16 is a side view showing how a bendable portion employed in the sixth embodiment is bent upward.

When a fluid is supplied into the fluid-pressure actuator 62 through a tube 63, the actuator 62 extends and the tension coil spring 61 contracts, as is shown in FIG. 16. As a result, the bendable portion 4 is bent upward.

Figure 17:
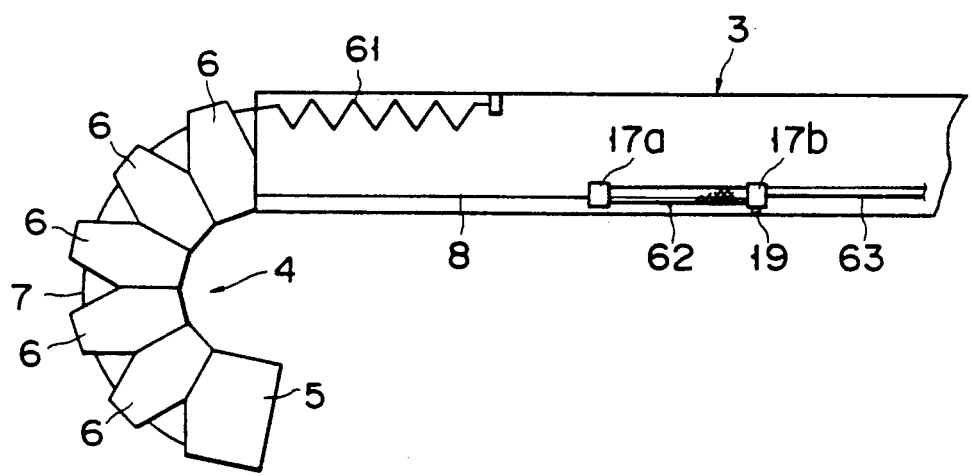
FIG. 17 is a side view showing how the bendable portion of the sixth embodiment is bent downward.

When the fluid is discharged from the actuator 62, the actuator 62 contracts, and the tension coil spring 61 extends, as is shown in FIG. 17. As a result, the bendable portion 4 is bent downward.

In the sixth embodiment, the tension coil spring 61 is employed in place of on actuator. Since the sixth embodiment employs a single actuator, only one tube is required. Accordingly, the diameter of the insertion section 2 can be reduced.

Figure 18:
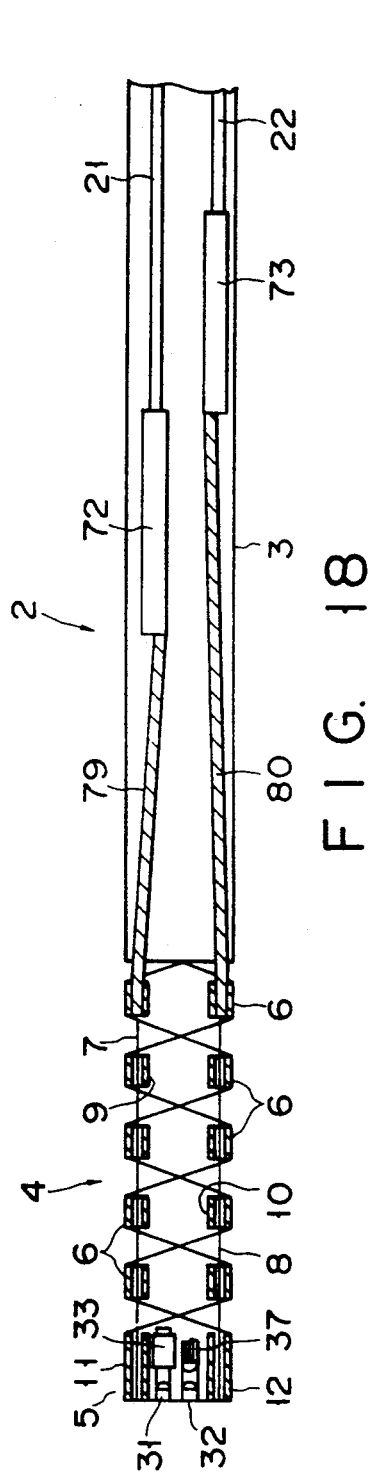
FIG. 18 a partially-sectional schematic side view of an insertion section employed in the seventh embodiment of the present invention

The seventh embodiment of the present invention will now be described, with reference to FIGS. 18 through 20.

In the seventh embodiment, a pair of upper and lower driving devices 72 and 73 are employed for pushing or pulling the operating wires 7 and 8. Each driving device is made up of: a long guide frame member 71 which is hollow and is formed of a semi-rigid material (i.e., a material which is elastic more or less); and a fluid-pressure actuator 13 (14) contained in the guide frame member 71. The fluid-pressure actuator 13 (14) is similar in structure to the actuators mentioned above. The upper and lower driving devices 72 and 73 are arranged in the insertion section 2 such that they are shifted from each other in the axial direction.

Figure 19:
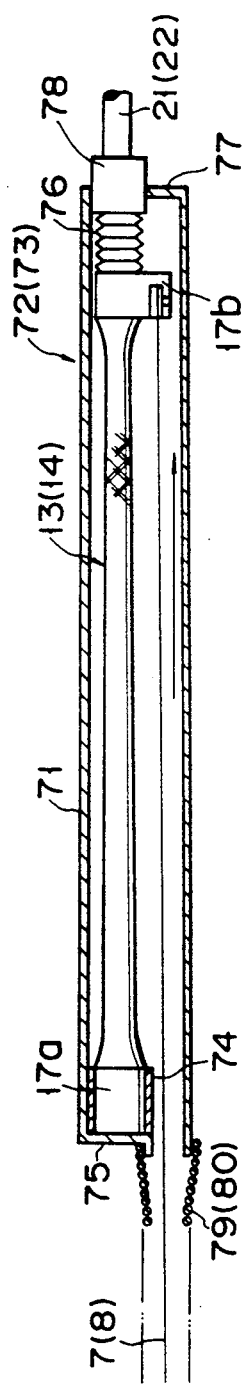
FIGS. 19 and 20 are sectional views of a fluid-pressure actuator mechanism employed in the seventh embodiment.
Figure 20:
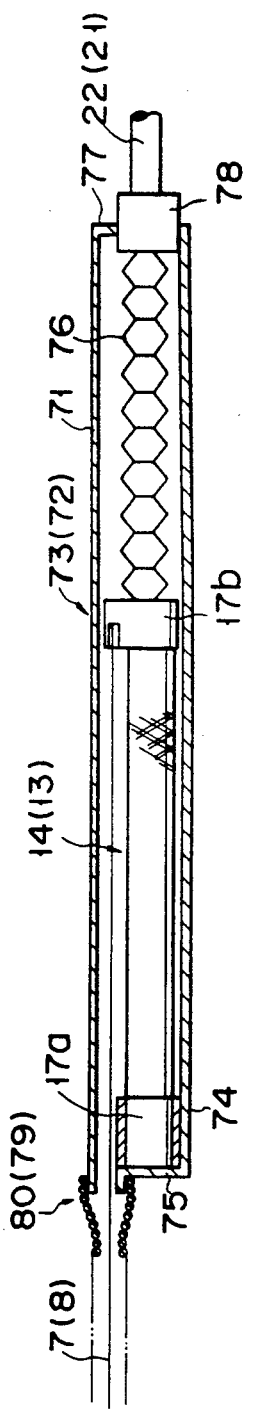

The driving devices 72 and 7 have such structures as are shown in FIGS. 19 and 20. Referring to FIGS. 19 and 20, the actuator 13 (14) is housed in the hollow section of the frame member 71. The front sealing member 17a located at the front end of the actuator 13 (14) is coupled to the front end wall 75 of the frame member 71, with a fixing tube 74 interposed therebetween, while the rear sealing member 17b located at the rear end (i.e., the free end) of the actuator 13 (14) is connected to one end of a bellows-like air tube 76. The other end of the air tube 76 is connected to the fluid supply/discharge tube 21 (22), through a mouthpiece 78 which extends through the rear end wall 77 of the frame member 71. The position at which the air tube 76 is connected to the fluid supply/discharge tube 21 (22) through the mouthpiece 78 is biased toward the center of the insertion section 2. The rear end of a tightly-wound coil sheath 79 (80) is coupled to the front end wall 75 of the frame member 71, either directly or with a connection pipe (not shown) interposed. The position at which the coil sheath 79 (80) is coupled to the front end wall 75 is biased toward the center of the insertion section 2. The front end of the coil sheath 79 (80) is fixed to the bending piece 6 located at the proximal end of the bendable portion 4. The operating wire 7 (8) is inserted through the coil sheath 79 (80), extends through the interior of the frame member 71 in parallel to the actuator 13 (14), and is coupled to the sealing member 17b located at the rear end of the actuator 13 (14). As for the other structures, the seventh embodiment is similar to the first embodiment.

When each fluid-pressure actuator 13 (14) is supplied with a pressurized fluid through tubes 76 and 21 (22), it extends. Since, therefore, the rear sealing member 17b is moved backward, the operating wire 7 (8) is pulled into the frame member 71. It should be noted that the coil sheath 79 (80) is a tightly-wound coil sheath and does not compress when the operating wire 7 (8) is being pulled.

When the fluid-pressure actuator 13 (14) of one driving device 72 (73) is made to extend, the corresponding operating wire 7 (8) is pulled, as is shown in FIG. 19, and the bendable portion 4 is bent, accordingly. Simultaneously, the fluid is discharged from the fluid-pressure actuator 13 (14) of the other driving device 72 (73). Thus, the actuator 13 (14) contracts and the bellows-like air tube 76 expands, as is shown in FIG. 20. When extending or contracting inside the frame members 71, the actuators 13 and 14 (in particular, the rear sealing members 17b thereof) slide along the inner wall of the frame members 71. Therefore, the actuators 13 and 14 hardly buckle inside the frame members 71. Incidentally, the frame member 71 need not be formed of a semi-rigid material; it may be formed of a rigid material, if so desired.

Figure 21:
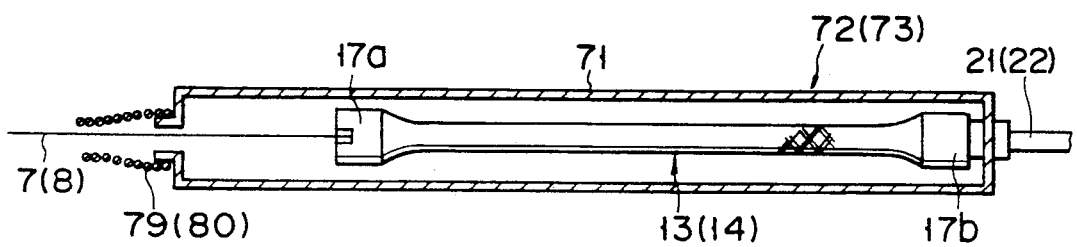
FIG. 21 shows the eighth embodiment of the present invention and is a sectional view illustrating a neutral state of a fluid-pressure actuator mechanism.

The eighth embodiment of the present invention will now be described, with reference to FIGS. 21 through 23.

Like the seventh embodiment, the eighth embodiment employs a pair of driving device 72 and 73, each of which is made up of a hollow frame member 71 and a fluid-pressure actuator 13 (14) contained in the frame member 71. The actuator 13 (14) is comprised of: an elastic member 15, a reinforcing mesh member 27, sealing members 17a and 17b, etc., as in the foregoing embodiments. The eighth embodiment differs from the seventh embodiment, only in that the operating wires 7 and 8 are connected to the sealing members 17a located at the front ends of the respective actuators 13 and 14, and that the actuators 13 and 14 are controlled to be extendible by $\frac{1}{2}$, as is understood in FIG. 21 showing the neutral state of the bendable portion 4.

Figure 22:
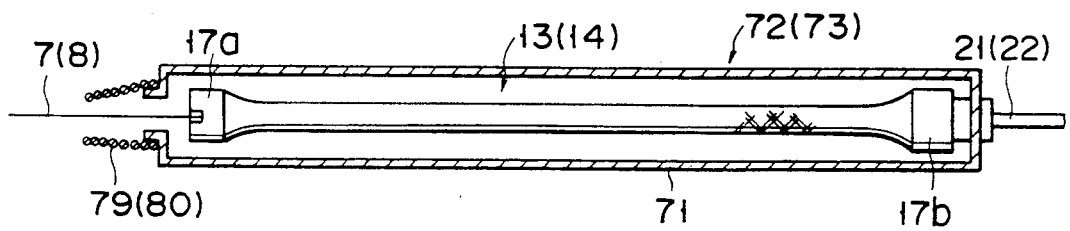
FIG. 22 also shows the eighth embodiment and is a sectional view illustrating an extended state of the actuator mechanism.
Figure 23:
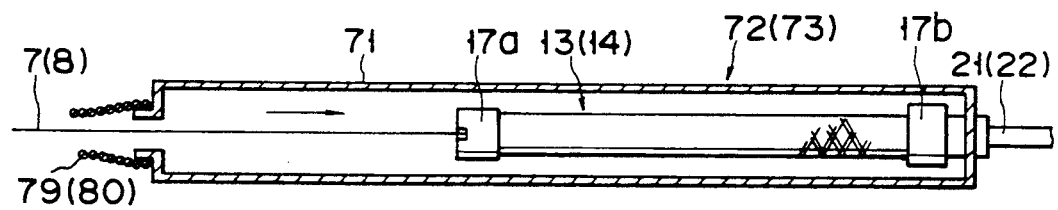
FIG. 23 also shows the eight embodiment and is a sectional view illustrating a contracted state of the actuator mechanism.

To bend the bendable portion 4, one of the fluid-pressure actuators 13 and 14 is supplied with a pressurized fluid, so that the actuator 13 (14) extends, pushing the operating wire 7 (8), as is shown in FIG. 22. Simultaneously, a pressurized fluid is discharged from the other actuator 14 (13), so that the actuator 14 (13) contracts and recovers its original shape, pulling the operating wire 8 (7), as is shown in FIG. 23. Therefore, the bendable portion 4 can be bent in accordance with the extension or contraction of the actuators 13 and 14. When extending or contracting inside the frame member 71, the actuators 13 and 14 (in particular, the front sealing members 17a thereof) slide along the inner wall of the frame members 71. Therefore, the actuators 13 and 14 hardly buckle inside the frame members 71.

Figure 24:
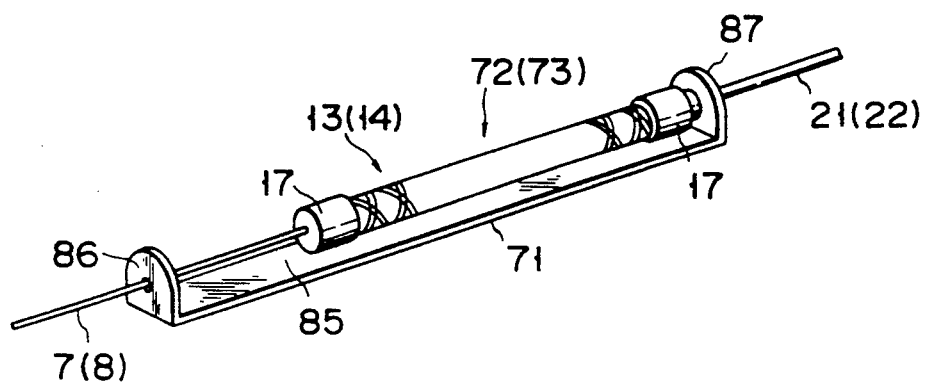
FIG. 24 is a perspective view showing one modification of the fluid-pressure actuator mechanism of the eighth embodiment.
Figure 25:
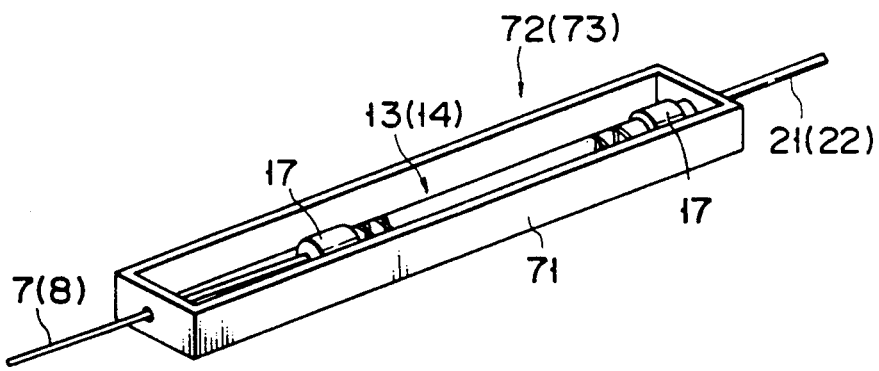
FIG. 25 is a perspective view showing another modification of the fluid-pressure actuator mechanism of the eighth embodiment.
Figure 26:
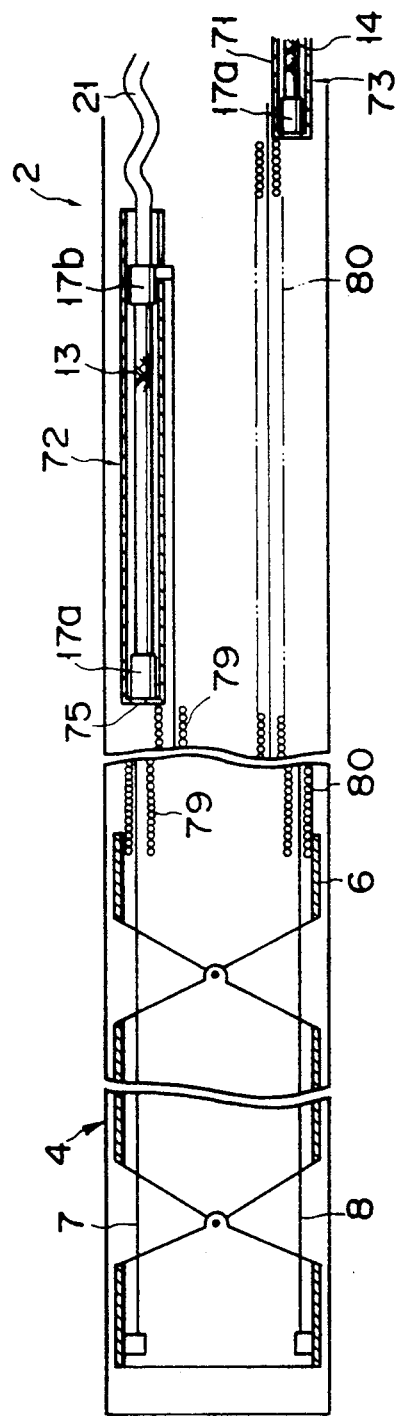
FIG. 26 is a schematic explanatory view of an endoscope's insertion section incorporating a fluid-pressure actuator according to the ninth embodiment of the present invention.

FIGS. 24 and 25 each show a modification of the driving devices (i.e., actuator mechanisms) 72 and 73 employed in the eighth embodiment. In the modified driving device 72 (73) shown in FIG. 24, the frame member 71 is made by a long plate member 85, and raised portions 86 and 87 are formed at the respective ends of the plate member 85. In the modified driving device 72 (73) shown in FIG. 25, the frame member 71 is in the form of a box one face of which is cut away. As may be understood from these modifications, the frame member 71 can be modified in various ways; it may be in the form of a coil, a curved tube, or the like.

The ninth embodiment of the present invention will now be described, with reference to FIGS. 26 through 29.

The ninth embodiment is considered a modification of the driving devices 72 and 73 employed in the seventh embodiment. Referring to FIGS. 26-29, the actuator 13 (14) is housed in the hollow section of the guide frame member 71. This frame member 71 is made by an elongated, soft tubular member. The front sealing member 17a located at the front end of the actuator 13 (14) is coupled to the front end wall 75 of the frame member 71, while the rear sealing member 17b located at the rear end (i.e., the free end) of the actuator 13 (14) is connected to a flexible fluid supply/discharge tube 21 (22), through a connection pipe 90. At the rear end of the actuator 13 (14), the elastic member 15, the reinforcing mesh member 27 and the fluid supply/discharge tube 21 (22) secured together by the same member, for example by the sealing member 17b or the connection pipe 90. The fluid supply/discharge tube 21 is set slack, so as not to obstruct the extension or contraction of the actuator 13 (14). In the ninth embodiment, the flexible fluid supply/discharge tube 21 (22) may be coiled, to provide it with an extension/contraction characteristic.

A coupling pin 92 protrudes from the sealing member 17b at the rear end of the actuator 13 (14), and a guide groove 92 is formed in the side wall of the frame member 71 in such a manner as to extend in the longitudinal direction of the frame member 71. The coupling pin 92 is inserted in the guide groove 92 and is projected from the outer surface of the frame member 71. The rear end of the operating wire 7 (8) is connected to the projected end of the coupling pin 92. In other words, the operating wire 7 (8) does not pass through the interior of the frame member 71; it is located in the outside of the frame member 71 and passes in parallel to its outer wall.

The rear end of a tightly-wound coil sheath 79 (80) is coupled to the front end wall 75 of the frame member 71, either directly or with a connection pipe (not shown) interposed. The position at which the coil sheath 79 (80) is coupled to the front end wall 75 is biased toward the center of the insertion section 2. The front end of the coil sheath 79 (80) is fixed to the bending piece 6 located at the proximal end of the bendable portion 4.

Inside the insertion section 2, the driving devices 72 and 73 are shifted from each other in the axial direction.

When each fluid-pressure actuator 13 (14) is supplied with a pressurized fluid through tubes 76 and 21 (22), it extends, as is shown in FIG. 29. Since, therefore, the rear sealing member 17b is moved backward, the operating wire 7 (8) is pulled backward. It should be noted that the coil sheath 79 (80) is a tightly-wound coil sheath and does not compress when the operating wire 7 (8) is being pulled.

When the fluid-pressure actuator 13 (14) of one driving device 72 (73) is made to extend, the corresponding operating wire 7 (8) is pulled, and the bendable portion 4 is bent, accordingly. Simultaneously, the fluid is discharged from the fluid-pressure actuator 14 (13) of the other driving device 73 (72). When extending or contracting inside the frame member 71, the actuators 13 and 14 (in particular, the rear sealing members 17b thereof) slide along the inner wall of the frame members 71. Therefore, the actuators 13 and 14 hardly buckle inside the frame member 71.

The tenth embodiment of the present invention will now be described, with reference to FIG. 30.

Figure 30:
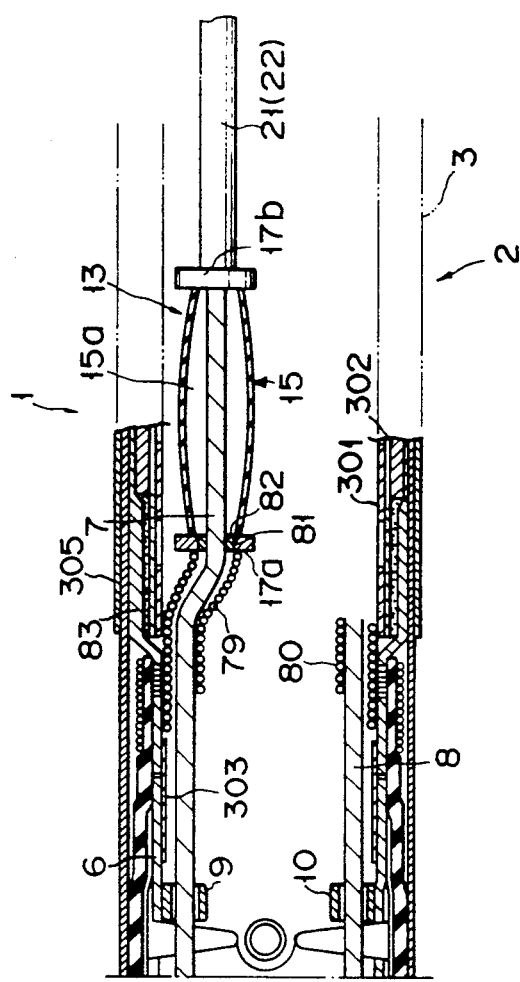
FIG. 30 is a schematic explanatory view of an endoscope's insertion section to which the tenth embodiment of the present invention is applied.

As is shown in FIG. 30, the insertion section 2 of an endoscope 1 is comprised of a flexible tube portion 3, a bendable portion 4 and a distal end portion 5. These portions are arranged from the proximal end of the insertion section 2 to the distal end thereof in the order mentioned, and are coupled together. The bendable portion 4 has a plurality of bending pieces 6, and the adjacent bending pieces 6 are pivotally coupled in such a manner as to be vertically rotatable relative to each other. Each bending piece 6 has upper and lower wire guides 9 and 10, and operating wires 7 and 8 used for bending the bendable portion 4 are inserted into the upper and lower winding guides 9 and 10, respectively. The foremost bending piece 6, located at the distal end of the bendable portion 4, is coupled to the main component of the distal end portion 5. The tip ends of upper and lower operating wires 7 and 8 are connected to the foremost bending piece 6 by fixing means, e.g., by soldering.

The flexible tube portion 3 (i.e., the proximal end portion of the insertion section 2) and the bendable portion 4 are coupled to each other by means of a coupling pipe 83. The flexible tube portion 3 and the bendable portion 4 can be detached from each other, for repair or maintenance. At one end, the coupling pipe 83 is fitted around a flexible joint tube 301 and a blade-like tube 302, which are parts of the flexible tube portion 3. The coupling pipe 83 is fixed to the tubes 301 and 302 by brazing, for example. At the other end, the coupling pipe 83 is connected, through a short tube 303, to the bending piece 6 arranged at the rearmost end of the bendable portion 4. The coupling pipe 83, the short tube 303 and the bending piece 6 are fixed to one another by brazing, for example. A fluid-pressure actuator 13 and guide pipes 79 and 80, which will be detailed below, are arranged such that they are exposed when the flexible tube portion 3 and the bendable portion 4 are disconnected from each other by melting the braze. Since the guide tubes 79 and 80 are attached to the coupling pipe 83, they can be pulled out of the insertion section 2, together with the coupling pipe 83.

Incidentally, reference numerals 304 and 305 in FIG. 30 denote blade-like sheath tubes, respectively.

The upper operating wire 7 connected to the foremost bending piece 6 is inserted through the upper guides 9 of the bending piece 6, is guided through a guide pipe 79 (which is made by a tightly-wound coil, and is flexible but incompressible), and is connected to the upper fluid-pressure actuator 13 located inside the flexible tube portion 3. Likewise, the lower operating wire 8 connected to the foremost bending piece 6 is inserted through the lower guides 10 of the bending piece 6, is guided through a guide pipe 80 (which is also made by a tightly-wound coil, and is flexible but incompressible), and is connected to the lower fluid-pressure actuator (not shown) located inside the flexible tube portion 3. The upper and lower actuators are shifted from each other in the axial direction of the insertion section 2.

As is shown in FIG. 30, the elastic member 15 of the fluid-pressure actuator 13 is a comparatively long tubular member formed of e.g. rubber, and the interior of the elastic member 15 defines an inner space 15a with reference to which a pressurized fluid is supplied or discharged. Front and rear sealing members 17a and 17b are coupled to the front and rear ends of the elastic member 15, respectively, to thereby seal the interior of the elastic member 15. An insertion hole 81 is formed in the front sealing member 17a.

Through the insertion hole 81, the operating wire 7 (8) is inserted into the elastic member 15. Inside the elastic member 15, the rear end of the operating wire 7 (8) is connected to the rear sealing member 17b. The operating wire 7 (8) is arranged coaxial with the elastic member 15; in other words, it extends along the central axis of the elastic member 15. An elastic 0-ring 82 is fitted in the insertion hole 81 of the front sealing member 17a. Due to the O-ring 82, the operating wire 7 (8) hermetically slides through the insertion hole 81, so that the internal space 15a of the elastic member 15 is hermetically sealed at all times.

Although not shown, the elastic member 15 is covered with a reinforcing mesh member, such as that described above. The reinforcing mesh member is obtained by interlacing warp and weft strands of inextensible element wires in a plain weave manner, for example, in such a manner that the interlaced warp and weft strands constitute a tubular structure. The element wires are interlaced such that they form the same angle with reference to the longitudinal axis of the elastic member 15. The front and rear ends of the reinforcing mesh member are attached to the front and rear sealing members 17a and 17b, respectively. The reinforcing mesh member provides the elastic member 15 with an extension force when the elastic member 15 is applied with a fluid pressure. If the element wires of the reinforcing mesh member are interlaced such that they form a wide angle with reference to the longitudinal axis of the elastic member 15, then the elastic member 15 can greatly decrease in diameter when it extends.

The front sealing member 17a is fixed to the rear end of the guide pipe 79 (80). The front end of this guide pipe 79 (80) is fixed to a stationary member provided on the inner wall of the insertion section 2. For example, the front end of the guide pipe 79 (80) is fixed to the inner wall of a joining pipe 83 which is used for joining the flexible tube portion 3 and the bendable portion 4 together. With this structure, the guide pipe 79 (80) constitutes a coupling member which is fixed to the inner wall of the insertion section 2.

The guide tube 79 (80), which is flexible but incompressible, holds the front sealing member 17a. With this structure, the front sealing member 17a is securely coupled to the stationary member provided on the inner wall of the insertion section 2, through the guide pipe 79 (80).

Due to the fixing structure mentioned above, the front sealing member 17a serves as a fixed end of the elastic member 15. It should be noted that any other fixing structure may be employed in place of that mentioned above, as long as the alternative fixing structure permits the front sealing member 17a to be securely held. For example, the front sealing member 17a may be fixed directly to the stationary member provided on the inner wall of the insertion section, or may be fixed thereto by means of a rod-like guide member.

Flexible fluid supply/discharge tubes 21 and 22 are connected to the respective rear sealing members 17b, so as to supply or discharge a pressurized fluid (e.g., pressurized air) from the elastic members 15. Each rear sealing member 17b has an air hole (not shown), through which the corresponding fluid supply/discharge tube and elastic member 15 communicate with each other.

Figure 3:
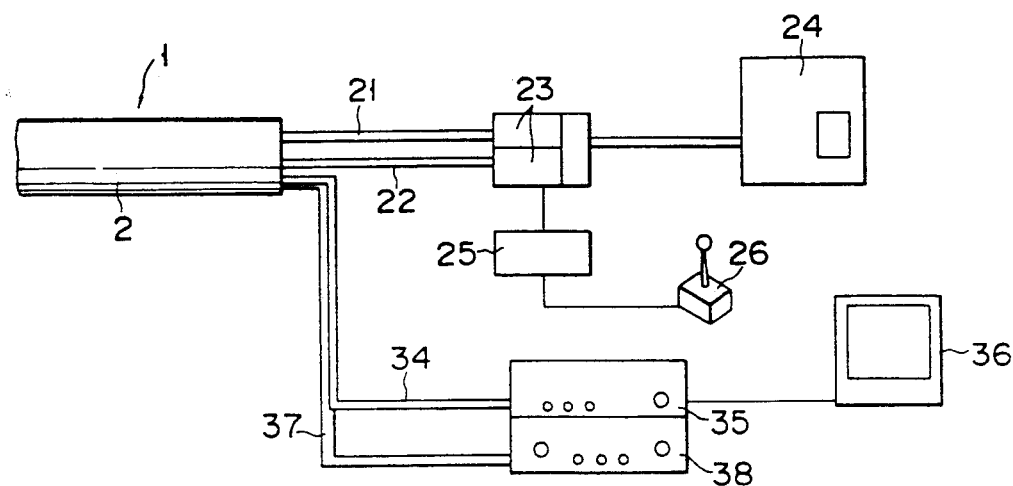
FIG. 3 is a schematic diagram showing an endoscope system to which the first embodiment of the present invention is applied.

As in the foregoing embodiments, the proximal end portions of the fluid supply/discharge tubes 21 and 22 extend through the interior of the insertion section 2 and are led out of the endoscope 1. In the outside of the endoscope 1, the tubes 21 and 22 are connected to a compressor 24 through respective directional control valves 23, as is shown in FIG. 3. The directional control valves 23 controls the fluid pressure which is to be applied to the internal spaces of the actuators 13 through the tubes 21 and 22. The directional control valves 23 are controlled by a control device 25, and an operating device 26 is connected to the control device 25.

A description will be given of the operation of the endoscope system obtained in accordance with the tenth embodiment.

The operator operates the operating device 26 and cause the control device 25 to control the directional control valves 23 in such a manner that pressurized air is supplied from the compressor 24 to one of the fluid-pressure actuators 13 and 14 through the fluid supply/exhaust tube 21 or 22. Due to the supply of the pressurized air, the pressure in the internal space 15a of the elastic member 15 increases, with the result that the elastic member 15 extends in the axial direction thereof and also expands in the radial direction. The axial extension of the elastic member 15 causes the rear sealing member 17b to slide backward. As a result, the operating wire 7 (8) connected to the rear sealing member 7b is pulled backward, and this pulling force is transmitted to the bendable portion 4, thus curving this bendable portion 4.

In the tenth embodiment, the elastic member 15 is not covered with a semi-rigid tubular cover member. Thus, the fluid-pressure actuator 13 is allowed to have a short diameter. If the elastic member 15 were covered with a semi-rigid tubular cover member, it would be pressed against it at the time of expansion. Since this state is not produced in the tenth embodiment, the elastic member 15 withstands long use.

Figure 31:
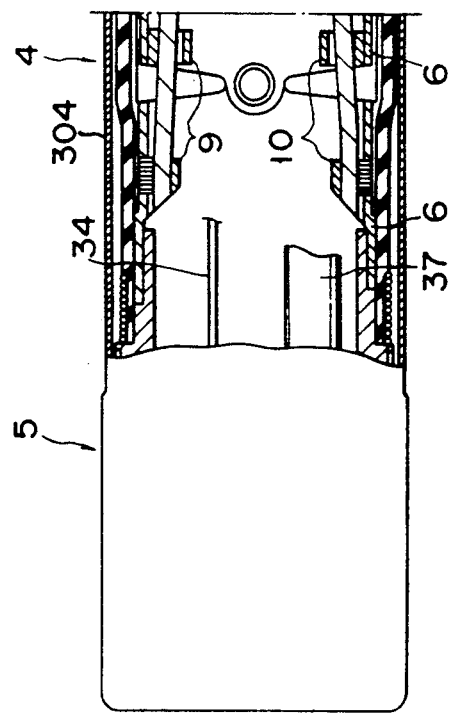
FIG. 31 is a longitudinally-sectional view of a fluid-pressure actuator employed in the eleventh embodiment of the present invention.
Figure 32:
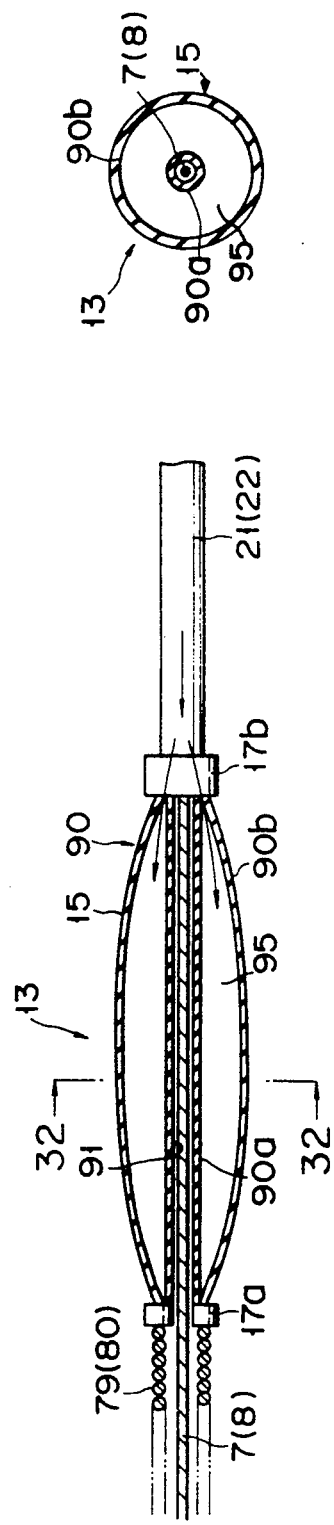
FIG. 32 is a sectional view taken along line 32—32 in FIG. 31.

The eleventh embodiment of the present invention will now be described, with reference to FIGS. 31 and 32.

In the fluid-pressure actuator 13 according to the eleventh embodiment, the elastic member 15 is constituted by an elastic double tube 90 made up of an outer elastic tube 90a and an inner elastic tube 90b. The inner elastic tube 90b is arranged inside the outer elastic tube 90a in such a manner as to provide an inner space 95 for the actuator 13. The inner elastic tube 90b has an inner region 91, through which the operating wire 7 (8) is inserted. With this structure, the inner space 95 of the actuator 13 is separate from the inner region 91 into which the operating wire 7 (8) is inserted. The inner region 91 of the inner elastic tube 90b extends in the axial direction of the elastic member 15, and is connected to the hole formed in each of the sealing members 17a and 17b. The rear end of the operating wire 7 (8) inserted through the inner region 91 of the inner tube 90b is coupled to the sealing member 17b located at the free end of the elastic member 15. As for the other structures, the eleventh embodiment is similar to the foregoing embodiments.

According to the eleventh embodiment, the inner region 91 through which the operating wire 7 (8) is inserted is kept away from the inner space 95 of the actuator 13. Thus, a seal member, such as the O-ring employed in the tenth embodiment, is not employed in the eleventh embodiment. In the eleventh embodiment, therefore, friction which may be caused by such a seal member is not produced, and the operating wires 7 and 8 may be of an ordinary type.

The twelfth embodiment of the present invention will now be described, with reference to FIGS. 33 through 37.

As is shown in FIG. 33, the endoscope 1 according to the twelfth embodiment is comprised of an insertion section 2, an operating section 103, and a universal cord 104. The operating section has an eyepiece portion 106, and the insertion section 2 has a distal end portion 5.

As is shown in FIG. 35, the housing of the distal end portion 5 is formed of metal or synthetic resin. The housing 111 is covered with a layer formed of rubber or synthetic resin. The housing 111 is made up of a circumferential wall 113, a front wall 114, and a rear wall 115, and an internal space 116 is defined by these walls.

A side-viewing observation window 117 is formed in the circumferential wall 113, and a direct-viewing observation window 118 is formed in the front wall 114. A tubular frame 121 extends through the rear wall 115. This tubular frame 121 holds the distal end of an optical fiber bundle 119 (i.e. an image guide) and objective lenses 120 which forms an image on the incident plane of the optical fiber bundle 119. The tip end portion of a protection tube 122, which covers the optical fiber bundle 122, is fitted around the rear end of the tubular frame 121.

A reflecting mirror 123 is arranged in the internal space 116 of the housing 111 such that it is located in front of the objective lenses 120. One end of the reflecting mirror 123 is pivotally coupled to a hinge pin 124 provided between the side-viewing and direct-viewing observation windows 117 and 118, so that the reflecting mirror is swingable. The objective lenses 120, the reflecting mirror 123, the side-viewing observation window 117 and the direct-viewing observation window 118 jointly constitute an objective optical system 125 of a vision field-switching type.

When the reflecting mirror 123 is at the position indicated in FIG. 35, the light entering the internal space 116 through the side-viewing observation window 117 is incident o the reflecting mirror 123 and reflected toward the objective lenses 120. When the reflecting mirror 123 is raised, the light entering the internal space 116 through the direct-viewing observation window 118 is incident directly on the objective lenses 120.

Normally, the reflecting mirror 123 is maintained at the position indicated in FIG. 35, by a positioning stopper (not shown), and urging means (not shown) for urging the reflecting mirror 123 to press it against the stopper. The urging means is made by e.g. a torsion spring wound around the hinge pin 124.

A wire 126, used for moving the reflecting mirror 123, is connected at one end to the free end of the reflecting mirror. The wire 126 is guided via a guide roller 127, passes via a through-hole 128 formed in the rear wall 115, and is connected at the other end to a driving mechanism 131 (which incorporates a fluid pressure type artificial muscle 130 and will be detailed later). The reflecting mirror 123 is swung by use of a driving force which is transmitted from the artificial muscle 130 through the wire 126.

Next, the driving mechanism 131 will be described. The driving mechanism 131 comprises: a long and hollow guide frame member 132 formed of either a rigid material or a semi-rigid material (i.e., a material which can be bent or curved more or less); and a fluid-pressure actuator 130 incorporated in the guide frame member 132. The wire 126 is pulled in accordance with the extension of the fluid-pressure actuator 130.

As is shown in FIG. 34, the fluid-pressure actuator 130 is made up of: a tubular elastic member 133 constituted by e.g. a rubber tube 133; a restricting mesh member (i.e., a mesh tube) 134 which surrounds the outer circumference of the tubular elastic member 133; and front and rear sealing members 135a and 135b for hermetically sealing the open ends of the tubular elastic member 133, respectively. The rear sealing member 135b has a hole 136 communicating with the internal space of the actuator 130. One end of a bellows tube 137, used for the supply or discharge of a fluid, is connected to the hole 136 of the rear sealing member 135b. As is shown in FIG. 35, the other end of the bellows tube 137 is connected to a connection mouthpiece 138 provided at the rear end of the guide frame member 132. Through the connection mouthpiece 138, the bellows tube 137 communicates with a flexible fluid supply/discharge tube 139.

The restricting mesh member 134 is obtained by interlacing warp strands 134a and weft strands 134b of inextensible element wires in a plain weave manner. The interlacing angle θ which each element wire (namely, a warp strand 134a or a weft strand 134b) forms with reference to the longitudinal axis of the actuator 130 is set to be greater than 54° 44', normally within the range of 65° to 80°. Therefore, the angle which is formed between a warp strand and a weft strand is expressed by 2θ.

Without the restricting mesh member 134, the fluid-pressure actuator 130 would radially expand, when its internal space is supplied with a fluid through the fluid supply/tube 139. However, such radial expansion is restricted by the restricting mesh members 134, and the actuator 130 extends in the axial direction thereof.

The front sealing member 135a of the fluid-pressure actuator 130 is fixed to the front end of the guide frame member 132, with a ring 140 interposed, while the rear sealing member 135b constitutes a free end which is slidable inside the guide frame member 132 while being guided by the inner wall of the guide frame member 132. The rear end of the mirror-operating wire 126 is coupled to the rear sealing member 135b (i.e., the free end of the actuator 130). Inside the guide frame member 132, the wire 126 and the actuator 130 are arranged in parallel to each other such that they do not obstruct each other.

The front end of the guide frame member 132 is fixed to the rear wall 115 of the housing 111 of the distal end portion 6, with a fixing member 141 interposed. A through-hole 142, which extends through both the fixing member 141 and the front end wall of the guide frame member 132, communicates with the through-hole 128 formed in the rear wall 115. Via these through-holes 128 and 142, the mirror-operating wire 126 is connected to the reflecting mirror 123.

The fluid supply/discharge tube 139 is guided to a power/light source device 150, by way of the interiors of the insertion section 2, the operation section 3 and the universal cord 4. Inside the power/light source device 150, the tube 139 is connected to an electromagnetic valve 151 (i.e., a fluid control device), and this valve 151 is connected to an air supply pump 152 (i.e., a fluid supply device) by means of an air supply pipe 159. The electromagnetic valve 151 is electrically connected to a switch 154 provided for the operation section 3 by means of a signal line 153 inserted in the universal cord 104. The electromagnetic valve 151 is controlled by operating the switch 154.

Figure 36:
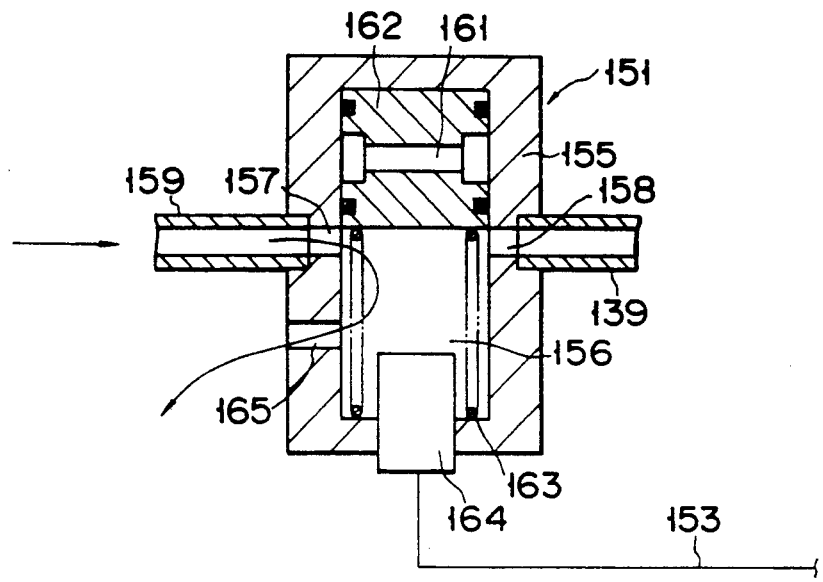
FIG. 36 is a longitudinally-sectional view of an electromagnetic valve employed in the twelfth embodiment.

The detailed structure of the electromagnetic valve 151 is shown in FIG. 36. As is shown in FIG. 36, the valve 151 has a valve casing 155, and the interior of this valve casing 155 defines a valve chamber 156. A first port 157 and a second port 158 are formed in the side wall of the valve casing 155 such that the first and second ports 157 and 158 face each other. The first port 157 is connected to the air supply pump 152 by means of the air supply pipe 159, as mentioned above, while the second port 158 communicates with the fluid-pressure actuator 130 of the driving mechanism 131 through the fluid supply/discharge tube 139.

Inside the valve chamber 156, a valve body 162 having a through-port 161 is arranged such that it is hermetically slidable in the vertical direction. The valve body 162 is urged upward by a urging spring 163. An electromagnet 164 is located in the bottom wall of the valve casing 155 such that the electromagnet 164 faces the bottom face of the valve body 162. A leak port 165 is formed in the side wall of the valve casing 155, so as to allow communication between the valve chamber 156 and the atmosphere.

When the switch 154 is on, the electromagnet 164 of the electromagnetic valve 151 is energized, thus attracting the valve body 162 to the electromagnet 164 against the urging force of the urging spring 163. As a result, the first and second ports 157 and 158 communicate with each other by way of the through-port 161 of the valve body 162. When the switch 154 is off, the electromagnet 164 is de-energized, thus allowing the valve body 162 to be raised by the urging force of the urging spring 163. As a result, the first and second ports 157 and 158 communicate with the leak port 165.

In the above manner, the electromagnet valve 151 is changed over in response to the ON or OFF operation of the switch 154, and the air supply pipe 159 communicates with either the fluid supply/discharge tube 139 or the atmosphere.

A description will now be given of the operation of the endoscope 1 of the twelfth embodiment.

The switch 154 is kept off at a normal time. Since, in this state, the electromagnet 164 of the electromagnetic valve 151 is de-energized, the valve body 162 is kept raised by the urging force of the urging spring 163, and the first and second ports 157 and 158 communicate with the leak port 165. Therefore, that fluid supplied into the valve chamber 156 leaks through the leak port 165 (which has a low flow-passage resistance) and thus discharges into the atmosphere. Since no pressurized fluid is supplied into the fluid-pressure actuator 130 of the driving mechanism 131, the actuator 130 is in a contracted state. In the contracted state of the actuator 130, the wire 126 is not pulled, and the reflecting mirror 123 is maintained at the position indicated in FIG. 35. In other words, the reflecting mirror 123 is slanted substantially 45° with reference to the vertical direction, and the light coming through the side-viewing observation window 11 is guided to the objective lenses 120, being reflected by the mirror 123.

Figure 37:
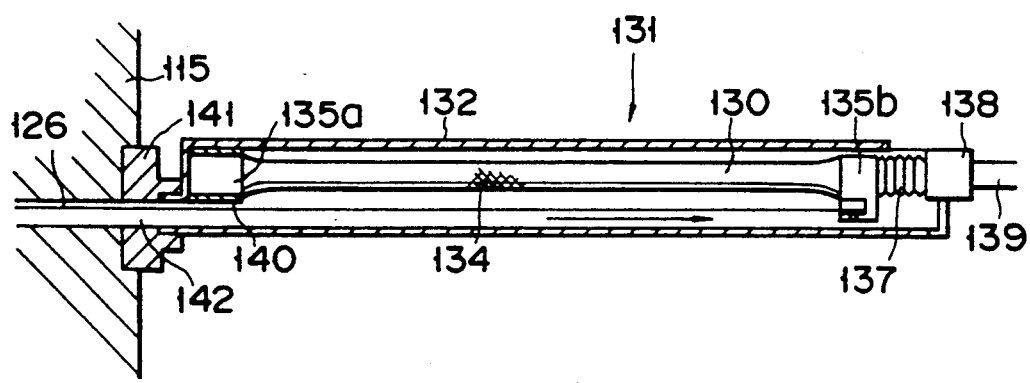
FIG. 37 is a longitudinally-sectional view illustrating an extended state of a fluid-pressure actuator employed in the twelfth embodiment.

When the switch 154 is turned on, the electromagnet 164 of the electromagnetic valve 151 is energized, thus attracting the valve body 162 against the urging force of the urging spring 163. As a result, the communication between the first and second ports 157 and 158 is established via the through-port 161 of the valve body 162. Simultaneously, the leak port 165 is closed by the valve body 162. Therefore, the pressurized fluid (e.g., pressurized air) sent by the air supply pump 152 is supplied into the fluid-pressure actuator 130 of the driving mechanism 131 by way of the fluid supply/discharge tube 139. Accordingly, the actuator 130 extends in the axial direction. In other words, the actuator 130 lengthens, as is shown in FIG. 37. Since, inside the guide frame member 132, the rear sealing member 135b slides backward in accordance with the axial extension of the actuator 130, the wire 126 coupled to the rear sealing member 135b is pulled backward. The wire 126 being pulled, the reflecting mirror 123 is swung upward with the hinge pin 124 as a center, in the direction indicated by the arrow in FIG. 35. Since, therefore, the reflecting mirror 123 is withdrawn from the optical path between the direct-viewing observation window 118 and the objective lenses 120, the light coming through the direct-viewing observation window 118 is guided to the objective lenses 120

In the twelfth embodiment, the fluid-pressure actuator 130 is guided by the inner wall of the guide frame member 132 when it extends axially. In addition, the rear sealing member 135b of that actuator 130 is also guided by the inner wall of the guide frame member 132 when it moves backward. Thus, the actuator 130 can extend in a reliable manner without buckling in the meantime. Moreover, the actuator 130 does not strongly touch or rub on the inner wall of the guide frame member 132.

According to the twelfth embodiment, a fluid is supplied or discharged from the fluid-pressure actuator 130 when the switch 154 is turned on or off. The actuator 130 axially extends or contracts in response to the supply or discharge of the fluid, and this axial extension or contraction is used for switching the reflecting mirror 123 between a side-viewing position and a direct-viewing position. With this structure, the operator can easily switch the endoscope 1 between a side-viewing mode and a direct-viewing mode.

The thirteenth embodiment of the present invention will now be described, with reference to FIGS. 38 and 39. In this embodiment, an extensible/contractible actuator is applied to a focus-adjusting mechanism which adjusts the focus of the objective optical system of an endoscope As is shown in FIG. 38, the tip end of an optical fiber bundle 119 (i.e., an image guide) is arranged in the distal end portion 5 of an insertion section 2. A fixing lens 171 is attached to the tip end face of the optical fiber bundle 119. Movable lenses 173, used for focus adjustment, are interposed between the fixing lens 171 and an observation window 172. These structural components jointly constitute a direct-viewing objective optical system. The movable lenses 173 are incorporated in a cylindrical lens frame 174. This lens frame 174 is fitted in a guide hole 175, which is formed inside the housing 111 of the distal end structure 5 to be coaxial with the objective optical system. To bring the focal point on the tip end face of the optical fiber bundle 119, the movable lenses 173 are moved in the direction of the optical axis, together with the lens frame 174.

The lens frame 174 is provided with a projection piece 176 which is projected from the predetermined portion of the lens frame 174. The projection piece 176 extend into region 177 through a guide groove formed in the wall of the housing 111. The projection piece 176 is connected to a fluid-pressure actuator 130 by means of coupling rod 181. The coupling rod 181 is made by e.g. an unbendable pipe and serves as a driving force-transmitting member. The fluid pressure actuator 130 has a similar structure to that of the above-mentioned actuators. The actuator 130 has a front sealing member 135a located at the front end thereof, and a rear sealing member 135b located at the rear end thereof. The front sealing member 135a is coupled to the coupling rod 181, while the rear sealing member 135b is secured to either the housing or a stationary member 182 provided in the insertion section 2. The actuator 130 and the coupling rod 181 are coaxially aligned with each other such that they are parallel to the optical axis of the objective lens system.

As for the structures not mentioned above, the thirteenth embodiment is similar to the foregoing embodiments.

In the thirteenth embodiment, the axial extension or contraction of the actuator 130 is utilized for adjusting the focal point of the objective lens system. To adjust the focal point of the objective lens system, the electromagnetic valve 151 is operated such that a pressurized fluid is supplied from the air supply pump 152 into the actuator 130 by way of the fluid supply/discharge tube 139. In response to the supply of the pressurized fluid, the actuator 130 extends in the axial direction, as is shown in FIG. 39A. The axial extension of the actuator 130 is transmitted to the lens frame 174 through the coupling rod 181, with the result that the movable lenses 173 are moved forward.

If the electromagnetic valve 151 is operated such that it stops the supply of the fluid into the actuator 130 and causes the fluid to discharge into the atmosphere, then the actuator 130 contracts in the axial direction, as is shown in FIG. 39B. The axial contraction of the actuator 130 is transmitted to the lens frame 174 through the coupling rod 181, with the result that the movable lenses 173 are moved backward.

The focal point of the objective optical system can be adjusted, with the movable lenses 134 being moved forward or backward in response to the axial extension or contraction of the actuator 130.

The lens frame 174 incorporating the movable lenses 173 could be moved by providing a knob for the operating section 3 and stretching a long operating wire between the lens frame 174 and the knob. This type of focus-adjusting structure could not ensure a reliable operation since the operating wire would be liable to slacken during use. The focus-adjusting structure obtained in accordance with the thirteenth embodiment does not employ such an operating wire, and is free from any problem arising from the use of such a wire. In addition, the focus-adjusting structure of the thirteenth embodiment is satisfactory in responsiveness, and thus ensures accurate focus adjustment.

The fourteenth embodiment of the present invention will now be described, with reference to FIGS. 40 through 42. In this embodiment, an extensible/contractible actuator is employed for varying the aperture of a diaphragm device which is incorporated in the objective optical system of an endoscope.

As is shown in FIG. 40, a solid-state imaging element 186 (e.g., a CCD) is arranged in the distal end portion 5 of an insertion section 2 in such a manner that the imaging element 186 faces an objective optical system 185. The light which enters the insertion section 2 through an observation window 187 is focused on the light-receiving face of the image element 186 by the objective optical system 185. A signal cable 188, which is used for the transmission of an image signal, is connected to the imaging element 186. This signal cable 188 is guided through the insertion section 2, an operation section 3 and a universal cord 4, and is connected to an external image processor (not shown).

The objective optical system 185 comprises a pair of focusing lenses 189, and a diaphragm device 190 located between the focusing lenses 189. The diaphragm device 190 controls the amount of light incident on the light-receiving face of the solid-state imaging element 185. As is shown in FIG. 41A, the diaphragm device 190 is made up of a diaphragm disk 192 and a diaphragm blade 193. The diaphragm disk 192 has a first opening 191 formed in the center thereof and having a comparatively large diameter, and the diaphragm blade 193 has a second opening 195 having a diameter smaller than that of the first opening. The diaphragm blade 193 is pivotally coupled to a pin 194 and is therefore swingable with the pin 194 as a center.

The diaphragm blade 193 is swingable between two positions. At one position, the diaphragm blade 193 is on the periphery of the diaphragm disk 192 and is away the first opening 191, as is shown in FIG. 41A. At the other position, it is in the center of the diaphragm disk 192 and its second opening 195 is within the range of the first opening 191, as is shown in FIG. 41B.

A tension spring 196 is stretched between the diaphragm disk 192 and the diaphragm blade 193. By this tension spring 196, the diaphragm blade 193 is urged to the position shown in FIG. 41A.

The diaphragm blade 193 has a coupling pin 197 at the free end thereof, and one end of a flexible coupling wire 198 is coupled to the coupling pin 197. The other end of the coupling wire 198 is inserted through a guide hole 199 formed in the diaphragm disk 192, passes through region 178 defined inside the wall of a housing 111, and is connected to a driving mechanism 180. This driving mechanism 180 incorporates a fluid-pressure actuator 130 which is similar to that employed in the thirteenth embodiment. A front sealing member 135a located at the front end of the actuator 130 is connected to the coupling wire 198, while a rear sealing member 135b located at the rear end of the actuator 130 is secured to either the housing 111 or a stationary member 182 provided in the insertion section 2.

The guide hole 199, through which the coupling wire 198 is inserted, is located at a peripheral portion which is opposite to that where the pin 194 is located, and the first opening 191 is located between the guide hole 199 and the pin 194. With this structure, the diaphragm blade 193 is swung to the center of the diaphragm disk 192, as is shown in FIG. 41B, when it is pulled by the coupling wire 198.

As for the structure not mentioned above, the fourteenth embodiment is similar to the foregoing embodiments.

Figure 42A:
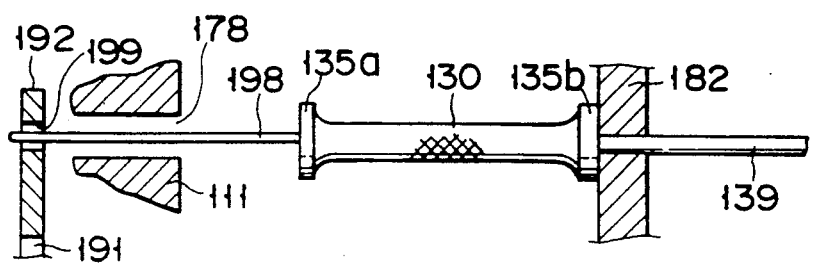
FIG. 42A and 42B are longitudinally-sectional views which show a fluid pressure actuator employed in the fourth embodiment, along its neighboring regions.

In the fourteenth embodiment, the axial extension or contraction of the fluid-pressure actuator 130 is used for changing the aperture of the diaphragm device 190 of the objective optical system 185. To change the aperture of the diaphragm device 190, the electromagnetic valve 151 is operated such that a pressurized fluid is supplied from the air supply pump 152 into the actuator 130 by way of the fluid supply/discharge tube 139. In response to the supply of the pressurized fluid, the actuator 130 extends in the axial direction, as shown in FIG. 42A. Since the actuator 130 pushes the coupling wire 198 when it extends axially, the diaphragm blade 193 is swung to the periphery of the diaphragm disk 192, being pulled by the tension spring 196. In other words, the diaphragm blade 193 is moved to the position shown in FIG. 41A, and does not overlap the first opening 191 of the diaphragm disk 192. Accordingly, the aperture of the diaphragm device 190 is determined by the diameter of the comparatively-large first opening 191.

Figure 42B:
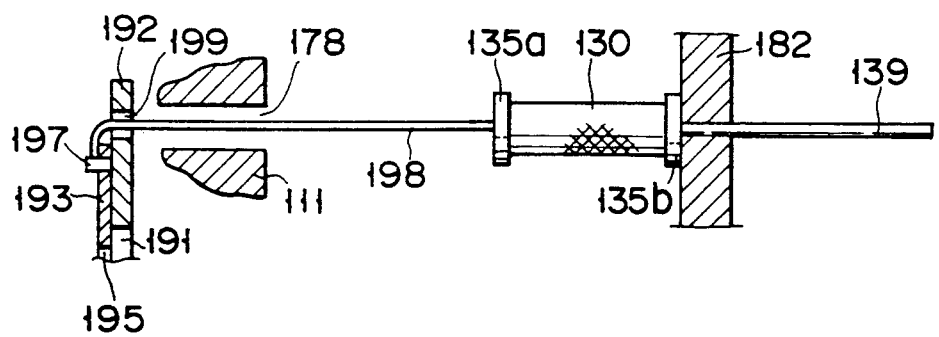

If the electromagnetic valve 151 is operated such that it stops the supply of the fluid into the actuator 130 and causes the fluid to discharge into the atmosphere, then the actuator 130 contracts in the axial direction, as is shown in FIG. 42B, due to the elasticity thereof (namely, the elasticity of the elastic member 133 and that of the restricting mesh member 134). Since the actuator 13 pulls the coupling wire 198 when it contacts axially, the diaphragm blade 193 is swung to the center of the diaphragm disk 192 against the pulling force the tension spring 196. In other words, the diaphragm blade 193 is moved to the position shown in FIG. 41B, and its second opening 195 is brought into the region within the first opening 191 of the diaphragm disk 192. Accordingly, the aperture of the diaphragm device 190 is determined by the diameter of the comparatively-small second opening 195.

The diaphragm blade 193 could be moved by providing a knob for the operating section 3 and stretching a long operating wire between the diaphragm blade 193 and the knob. This type of aperture controller could not ensure a reliable operation since the operating wire would be liable to slacken during use. The aperture controller obtained in accordance with the fourteenth embodiment does not employ such an operating wire, and is free from any problem arising from the use of such a wire. In addition, the aperture controller of the fourteenth embodiment is satisfactory in responsiveness, and thus ensures accurate aperture control. Further, it can be applied even to an endoscope whose insertion section is long. In comparison with a case where an electric motor or an electromagnet is employed, the aperture controller according to the fourteenth embodiment is simple in structure and small in size. The fluid-pressure actuator 130 is thin and long, and can be easily installed in the insertion section 2 of the endoscope 1. It should be also noted that since the actuator 130 greatly extends in the axial direction, it is not necessary to increase the degree of axial extension so as to driven the diaphragm blade 193. Accordingly, the aperture controller incorporating the actuator does not result in an increase of the size of the endoscope.

Figure 43:
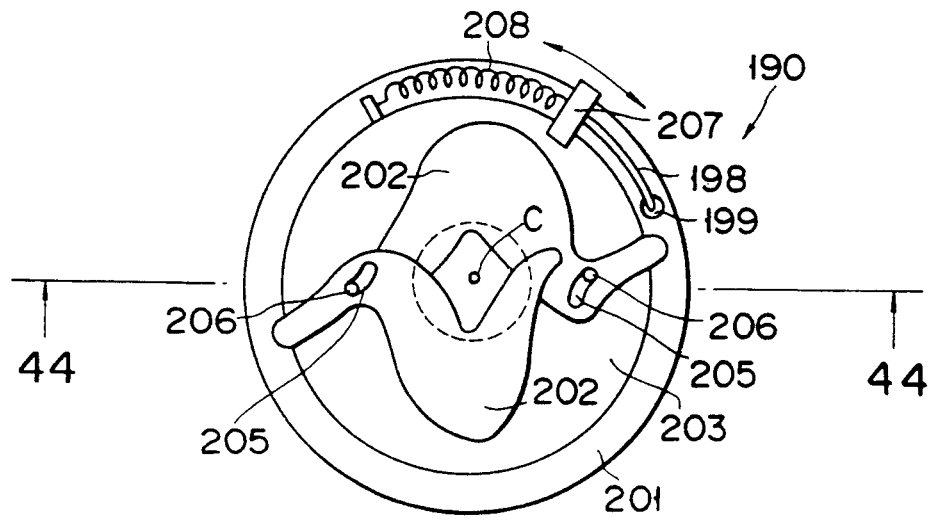
FIG. 43 is a front view of a diaphragm device, which is one modification of the fluid-pressure actuator of the fourteenth embodiment.
Figure 44:
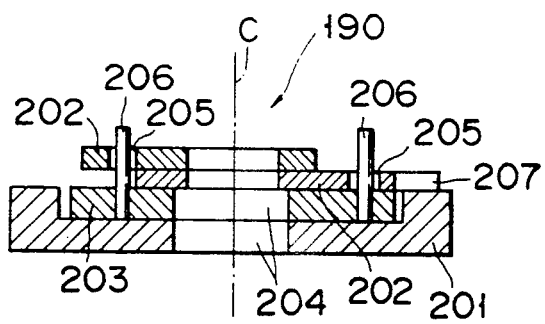
FIG. 44 is a sectional view of the diaphragm device, taken along line 44—44 in FIG. 43.

FIGS. 43 and 44 show one modification of the diaphragm device 190 of the fourteenth embodiment.

As is shown in FIGS. 43 and 44, the diaphragm device 190 according to this modification is of a so-called iris diaphragm type and comprises: a stationary ring 201; a rotatable ring 203 coaxially stacked on the stationary ring 201; and a plurality of diaphragm blades 202 which are pivotally coupled at one end to the stationary ring 201 and are swingable in accordance with the rotation of the rotatable ring 203. The stationary and rotatable rings 201 and 203 have holes 204, respectively, and the central axes of these holes 204 are aligned with the optical axis C of the objective optical system 185. The holes 204 jointly constitute a field diaphragm.

A cam hole 205 is formed in the proximal end portion of each diaphragm blade 202. Operating pins 203 are projected from the rotatable ring 203 such that they are fitted in the cam holes 205 of the diaphragm blades 202. A coupling pin 207 is attached to the rotatable ring 203, and one end of a flexible coupling wire 198 (which is similar to that mentioned above) is connected to the coupling pin 207. The other end of the coupling wire 198 is inserted through a guide hole 199 formed in the stationary ring 203, passes through region 178 defined inside the wall of a housing 111, and is connected to a fluid-pressure actuator 130.

A tension spring 208 is connected at one end to the coupling pin 207 of the rotatable ring 203, and is fixed to the predetermined point on the stationary ring 201. The tension spring 208 pulls the coupling pin 207 in such a manner that the diaphragm blades 193 defines an opening in the center of the diaphragm device 190.

According to this modification, the axial extension or contraction of the fluid-pressure actuator 130 is used for operating the diaphragm device 190. More specifically, when the actuator 130 extends axially, the rotatable ring 203 is pulled by the tension spring 208, and the diaphragm blades 202 are moved such that the opening defined by them becomes smaller. Conversely, when the actuator 130 contracts axially, the rotatable ring 203 is pulled by the coupling wire 198 against the pulling force of the torsion spring 208, and the diaphragm blades 202 are moved such that the opening defined by them becomes larger.

Figure 45:
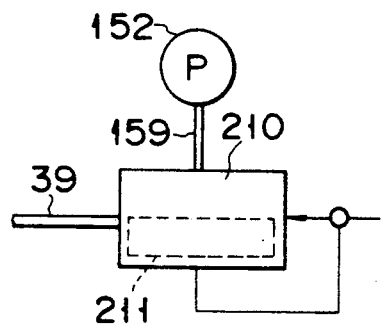
FIG. 45 is a schematic explanatory view showing one modification of an electromagnetic valve employed in the fourteenth embodiment.

In the case of the thirteenth and fourteenth embodiments and their modifications, the valve shown in FIG. 45 may be employed, in place of the electromagnetic valve mentioned above.

The valve shown in FIG. 45 is a servo valve 210 capable of controlling the pressure of the air which is supplied from an air supply pump 152 to a fluid-pressure actuator 130 through a liquid supply/discharge tube 139. When the servo valve 210 is supplied with an operation signal indicating the air pressure to be applied to the actuator 130, a pressure sensor 211 incorporated in the servo valve 210 feeds an output back such that the air is supplied into the actuator with constant pressure.

The actuator 130 extends or contracts in proportion to the air pressure applied thereto. Since the length of the actuator 130 can be varied steplessly, the focus adjustment, the aperture control, or the like can be executed in a stepless fashion.

The fluid to be supplied into the fluid-pressure actuator need not be a gas. A liquid, such as water or oil, may be used, instead.

According to the present invention, a driving device, which is used for bending the bendable portion of the insertion section of an endoscope or for driving an optical mechanism (e.g., a diaphragm device) employed in the endoscope, incorporates a fluid-pressure actuator which axially extends in response to the supply of a fluid thereto. Due to the incorporation of such an actuator, the driving device is simple in structure and can be installed in the endoscope without requiring a complicated mechanism. The actuator extends only in the axial direction. Therefore, the actuator does not restrict the installation spaces of other structural components of the endoscope, nor does it touch or rub on other structural components. In addition, the insertion section incorporating the actuator can be as thin as possible.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. An endoscope comprising:
   an elongated insertion section including a distal end portion, a proximal end portion, and a bendable portion located between the distal and proximal end portions;
   a fluid-pressure actuator, coupled to the insertion section, for bending the bendable portion, said fluid-pressure actuator including: (a) an extensible body defining an internal space and having an extension axis along which the extensible body extends or contracts; and (b) expansion-restricting means for restricting expansion of the extensible body, said expansion-restricting means causing the extensible body to extend in the direction of the extension axis when a fluid is supplied into the internal space, and causing the extensible body to contract in the direction of the extensible axis when the fluid is discharged from the internal space;
   conversion means for converting the extension or contraction of the fluid-pressure actuator into a bending motion of the bendable portion of the insertion section; and
   fluid supply/discharge means for supplying the fluid into the internal space of the extensible body or discharging the fluid from the internal space.

2. An endoscope according to claim 1, wherein said extensible body includes an elastic tube, and sealing members attached to respective ends of the elastic tube.

3. An endoscope according to claim 1, wherein said expansion-restricting means includes a mesh tube which is obtained by interlacing inextensible warp strands and inextensible weft strands, each of said warp and weft strands forming an interlacing angle $\theta$ of not less than 54° 44' with reference to the extension axis.

4. An endoscope according to claim 2, wherein said expansion-restricting means includes a mesh tube, both ends of which are coupled to said sealing members, respectively.

5. An endoscope according to claim 1, wherein said fluid-pressure actuator is arranged in said insertion section, and has a first end secured to the insertion section and a second end serving as a free end, said conversion means being coupled to the second end of the fluid-pressure actuator 6. An endoscope according to claim 5, wherein said fluid-pressure actuator is located closer to the proximal end portion than the bendable portion, said second end of the fluid-pressure actuator is oriented toward the bendable portion and said first end of the fluid-pressure actuator is oriented toward the proximal end portion of the insertion section, and said conversion means is coupled to the second end of the fluid-pressure actuator.

7. An endoscope according to claim 5, further comprising:
a frame, which surrounds the fluid-pressure actuator, for guiding the extension or contraction of the fluid-pressure actuator, said frame being connected to said first end of the fluid-pressure actuator;
an incompressible sheath for coupling the frame and the insertion section; and
an operating wire inserted through the sheath and connecting the conversion means to the second end of the fluid-pressure actuator.

8. An endoscope according to claim 7, wherein sad operating wire is arranged in the frame.

9. An endoscope according to claim 7, wherein said operating wire is arranged outside of the frame and extends in parallel to the fluid-pressure actuator.

10. An endoscope according to claim 5, wherein said fluid-pressure actuator is located closer to the proximal end portion than the bendable portion, said first end of the fluid-pressure actuator is oriented toward the bendable portion and said second end of the fluid-pressure actuator is oriented toward the proximal end portion of the insertion section, and said conversion means is coupled to the second end of the fluid-pressure actuator.

11. An endoscope according to claim 10, further comprising:
an operating wire for transmitting a driving force to the conversion means, said operating wire extending through the fluid-pressure actuator and being coupled to the second end of the fluid-pressure actuator.

12. An endoscope according to claim 11, wherein said extensible body of the fluid-pressure actuator includes a first elastic tube, and a second elastic tube inserted in the first elastic tube, said first and second elastic tubes defining said internal space therebetween, and said operating wire is inserted through the interior of the second elastic tube.

13. An endoscope according to claim 11, further comprising:
an incompressible sheath having a first end secured to the insertion section and a second end secured to the second end of the fluid-pressure actuator, said sheath containing the operating wire extending therethrough.

14. An endoscope according to claim 10, further comprising:
an operating wire for transmitting a driving force to the conversion means, said operating wire extending through a side region of the fluid-pressure actuator and being coupled to the second end of the fluid-pressure actuator.

15. An endoscope according to claim 1, wherein said elongated insertion section includes a longitudinal axis, and said fluid-pressure actuator is arranged on an outer wall of the insertion section and is parallel to the longitudinal axis of the insertion section.

16. An endoscope according to claim 15, wherein said fluid-pressure actuator is detachable from the insertion section.

17. An endoscope according to claim 1, wherein said fluid supply/discharge means includes:
a compressor;
a fluid passage which allows communication between the compressor and the internal space of the fluid-pressure actuator; and
a valve for opening/closing the fluid passage 18. An endoscope according to claim 17, wherein said fluid passage includes a tube which extends or contracts in the longitudinal direction thereof.

19. An endoscope according to claim 1, further comprising:
a second fluid-pressure actuator which is shifted from said fluid-pressure actuator in the direction of a longitudinal axis of the insertion section,
said second fluid-pressure actuator including:
an extensible body defining an internal space and having an extension axis along which the extensible body extends or contracts; and
expansion-restricting means for restricting expansion of the extensible body, said expansion-restricting means causing the extensible body to extend in the direction of the extension axis when a fluid is supplied into the internal space, and causing the extensible body to contract in the direction of the extensible axis when the fluid is discharged from the internal space.

20. An endoscope according to claim 1, further comprising:
a torsion spring, connected to the conversion means, for pulling the conversion means against a force which is produced by the contraction of the fluid-pressure actuator.

21. An endoscope comprising:
an elongated insertion section including a distal end portion, a proximal end portion, and a bendable portion located between the distal and proximal end portions;
a fluid-pressure actuator for bending the bendable portion, said fluid-pressure actuator including: (a) an extensible body defining an internal space and having an extension axis along which the extensible body extends or contracts; and (b) expansion-restricting means for restricting expansion of the extensible body, said expansion-restricting mean causing the extensible body to extend in the direction of the extension axis when a fluid is supplied into the internal space, and causing the extensible body to contract in the direction of the extensible axis when the fluid is discharged from the internal space, said fluid-pressure actuator being arranged in the bendable portion of the insertion section and in parallel to a longitudinal axis of the insertion section, said fluid-pressure actuator having a first end coupled to a tip end of the insertion section and a second end coupled to a rear end of the bendable portion, said fluid-pressure actuator converting the extension or contraction of the fluid-pressure actuator into a bending motion of the bendable portion; and
fluid supply/discharge means for supplying the fluid into the internal space of the extensible body or discharging the fluid from the internal space.

22. An endoscope comprising:
an insertion section including a distal end portion and a proximal end portion;
an optical system arranged in the insertion section and including an operatable portion;
a fluid-pressure actuator for driving the operatable portion of the optical system, said fluid-pressure actuator including: (a) an extensible body defining an internal space and having an extension axis along which the extensible body extends or contracts; and (b) expansion-restricting means for restricting expansion of the extensible body, said expansion-restricting means causing the extensible body to extend in the direction of the extension axis when a fluid is supplied into the internal space, and causing the extensible body to contract in the direction of the extensible axis when the fluid is discharged from the internal space;

conversion means for converting the extension or contraction of the fluid-pressure actuator into a motion of the operatable portion of the optical system; and fluid supply/discharge means for supplying the fluid into the internal space of the extensible body or discharging the fluid from the internal space.

23. An endoscope according to claim 22, wherein said extensible body includes a tubular elastic member, and sealing members attached to respective ends of the elastic member.

24. An endoscope according to claim 23, wherein said expansion-restricting means includes a mesh tube, both ends of which are coupled to the sealing members, respectively.

25. An endoscope according to claim 22, wherein said expansion-restricting means includes a mesh tube which is obtained by interlacing inextensible warp strands and inextensible weft strands, each of said warp and weft strands forming an interlacing angle $\theta$ of not less than 54° 44' with reference to the extension axis.

26. An endoscope according to claim 22, wherein said operatable portion of the optical system includes a mirror which is swingable and switches the endoscope from one observation field to another and which is driven by said fluid-pressure actuator.

27. An endoscope according to claim 22, wherein said operatable portion of the optical system includes a focus-adjusting mechanism for adjusting a focus of an objective lens said focus-adjusting mechanism being driven by said fluid-pressure actuator.

28. An endoscope according to claim 22, wherein said operatable portion of the optical system includes a diaphragm mechanism driven by said fluid-pressure actuator.

29. An endoscope according to claim 22, wherein said fluid-pressure actuator is arranged in said insertion section, and has a first end secured to the insertion section and a second end serving as a free end, said conversion means being coupled to the second end of the fluid-pressure actuator.

30. An endoscope according to claim 29, further comprising:

frame, which surrounds the fluid-pressure actuator, for guiding the extension or contraction of the fluid-pressure actuator, said frame being coupled to both the insertion and the first end of the fluid-pressure actuator; and an operating wire inserted through the frame and connecting the conversion means to the second end of the fluid-pressure actuator.

31. An endoscope comprising:

an elongated insertion section including a distal end portion, a proximal end portion, a bendable portion located between the distal and proximal end portions, and a base portion located between the bendable portion and the proximal end portion, said bendable portion and said base portion being detachably coupled to each other;

fluid-pressure actuator means, at least part of which is arranged inside the base portion, for bending the bendable portion, said fluid-pressure actuator means defining an internal space therein, said fluid-pressure actuator means axially extending when a fluid is supplied into the internal space, and axially contracting when the fluid is discharged from the internal space, said fluid-pressure actuator means having a first end which is fixed to a proximal end of the bendable portion, and a second end which is located inside the base portion and serves as a free end;

conversion means for converting the axial extension or contraction of the fluid-pressure actuator means to a bending motion of the bendable portion; and fluid supply/discharge means for supplying the fluid into the internal space of the fluid-pressure actuator means or discharging the fluid from the internal space.

32. An endoscope according to claim 31, wherein said fluid-pressure actuator means includes a plurality of fluid-pressure actuators arranged inside the insertion section.

33. An endoscope according to claim 32, wherein at least one of said fluid-pressure actuators is located closer to the proximal end portion than the other fluid-pressure actuators.

34. An endoscope according to claim 33, wherein said at least one fluid-pressure actuator has a first end coupled to a sheath which is connected to the insertion section, said sheath is axially incompressible but bendable, and said conversion means includes a wire inserted through the sheath, and one end of said wire is coupled to a tip end of the bendable portion, while the other end thereof is coupled to a free second end of said at least one fluid-pressure actuator.

35. An endoscope according to claim 32, further comprising:

a frame, which surrounds each fluid-pressure actuator, for guiding the extension or contraction of the fluid-pressure actuator, said frame being connected to said first end of the fluid-pressure actuator;

an incompressible sheath for coupling the frame and the insertion section; and an operating wire inserted through the sheath and connecting the conversion means to the second end of the fluid-pressure actuator.

* * * * *